(12) United States Patent
Bergeron et al.

(10) Patent No.: US 6,500,460 B1
(45) Date of Patent: Dec. 31, 2002

(54) FORMULATIONS FOR THE PREVENTION OR THE TREATMENT OF DISEASES AFFECTING MUCOSAE OR SKIN, OR FOR PREGNANCY PREVENTION, AND AN APPLICATOR FOR THE DELIVERY OF TOPICAL FORMULATIONS INTO MUCOSAL CAVITIES

(75) Inventors: Michel G. Bergeron, Québec (CA); André Désormeaux, Neufchatel (CA); Rabeea F. Omar, Sainte-Foy (CA); Julianna Juhasz, Québec (CA)

(73) Assignee: Infection-Recherche Inc., Quebec (CA)

( * ) Notice: Subject to any disclaimer, the term of this patent is extended or adjusted under 35 U.S.C. 154(b) by 0 days.

(21) Appl. No.: 09/693,289

(22) Filed: Oct. 20, 2000

Related U.S. Application Data

(63) Continuation of application No. PCT/CA99/00359, filed on Apr. 21, 1999.

(30) Foreign Application Priority Data

Apr. 21, 1998 (CA) ............................................ 2235427
Dec. 23, 1998 (CA) ............................................ 2257001

(51) Int. Cl.⁷ ................................................. A61K 9/14
(52) U.S. Cl. ...................................................... 424/486
(58) Field of Search ......................................... 424/486

(56) References Cited

U.S. PATENT DOCUMENTS

| | | | |
|---|---|---|---|
| 2,683,456 A | 7/1954 | Pierson | |
| 4,991,777 A | 2/1991 | Sato | |
| 5,843,043 A | 12/1998 | Markus | |

FOREIGN PATENT DOCUMENTS

| | | | |
|---|---|---|---|
| DE | 3513645 | | 10/1986 |
| EP | 0139855 | | 5/1985 |
| EP | 90302256.4 | | 9/1990 |
| EP | 0761246 | | 8/1996 |
| FR | 2585575 | * | 2/1987 |
| WO | WO9300114 | * | 1/1993 |
| WO | WO97/42962 | | 11/1997 |
| WO | WO9944631 | * | 9/1999 |
| WO | WO9953987 | * | 10/1999 |

* cited by examiner

*Primary Examiner*—William R. A. Jarvis
*Assistant Examiner*—Vickie Kim
(74) *Attorney, Agent, or Firm*—Nicholas A. Kees; Godfrey & Kahn, S.C.

(57) ABSTRACT

This invention relates to formulations for the prevention of infection and/or abnormal conditions of mucosae and/or skin caused by any pathogen and/or any disease, and more particularly for the prevention of sexually transmitted infections specially HIV and HSV. This invention also relates to formulations for the treatment of infection and/or abnormal conditions of skin and/or mucosae and more particularly for the treatment of herpetic lesions. The formulations could be used as a prophylactic agent to prevent accidental infection of health care workers. The formulations could be used for the healing and/or treatment of burn wounds and prevention of further infection. This invention also relates to the development of a unique vaginal/ano-rectal applicator for the uniform delivery of any topical formulations to treat and/or prevent any infection and/or abnormal conditions of mucosa cavity caused by any pathogen and/or disease.

7 Claims, 24 Drawing Sheets

LEGEND: —○— INFECTIVITY OF VIRUS INCUBATED WITH SLS (PANEL A) OR DS (PANEL B) (NO PRETREATMENT)
—●— INFECTIVITY OF VIRUS INCUBATED WITH SLS (PANEL A) OR DS (PANEL B) (1 h PRETREATMENT)

LEGEND: —○— INFECTIVITY OF VIRUS INCUBATED WITH SLS (PANEL A) OR DS (PANEL B) (NO PRETREATMENT)
—●— INFECTIVITY OF VIRUS INCUBATED WITH SLS (PANEL A) OR DS (PANEL B) (1 h PRETREATMENT)

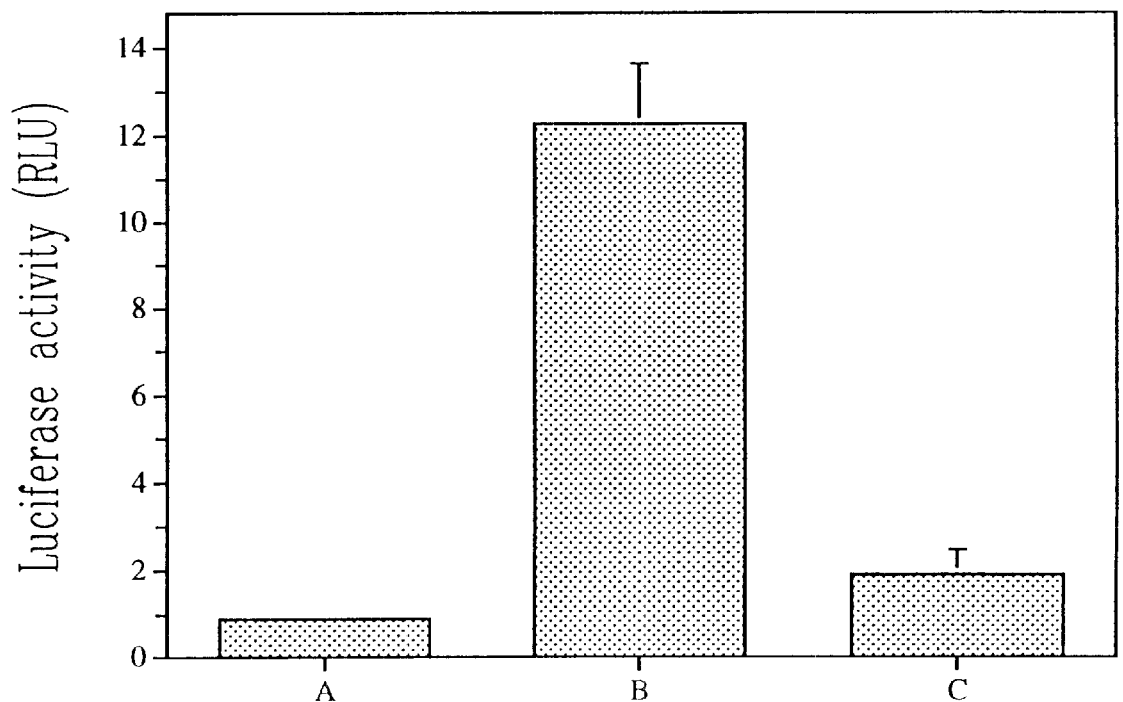

| SLS concentration (μM) | Percentage of control |
|---|---|
| 0 (EMEM) | 100 |
| 12.5 | 120.6 |
| 25 | 123.8 |
| 50 | 114.3 |
| 75 | 65.1 |
| 100 | 34.9 |

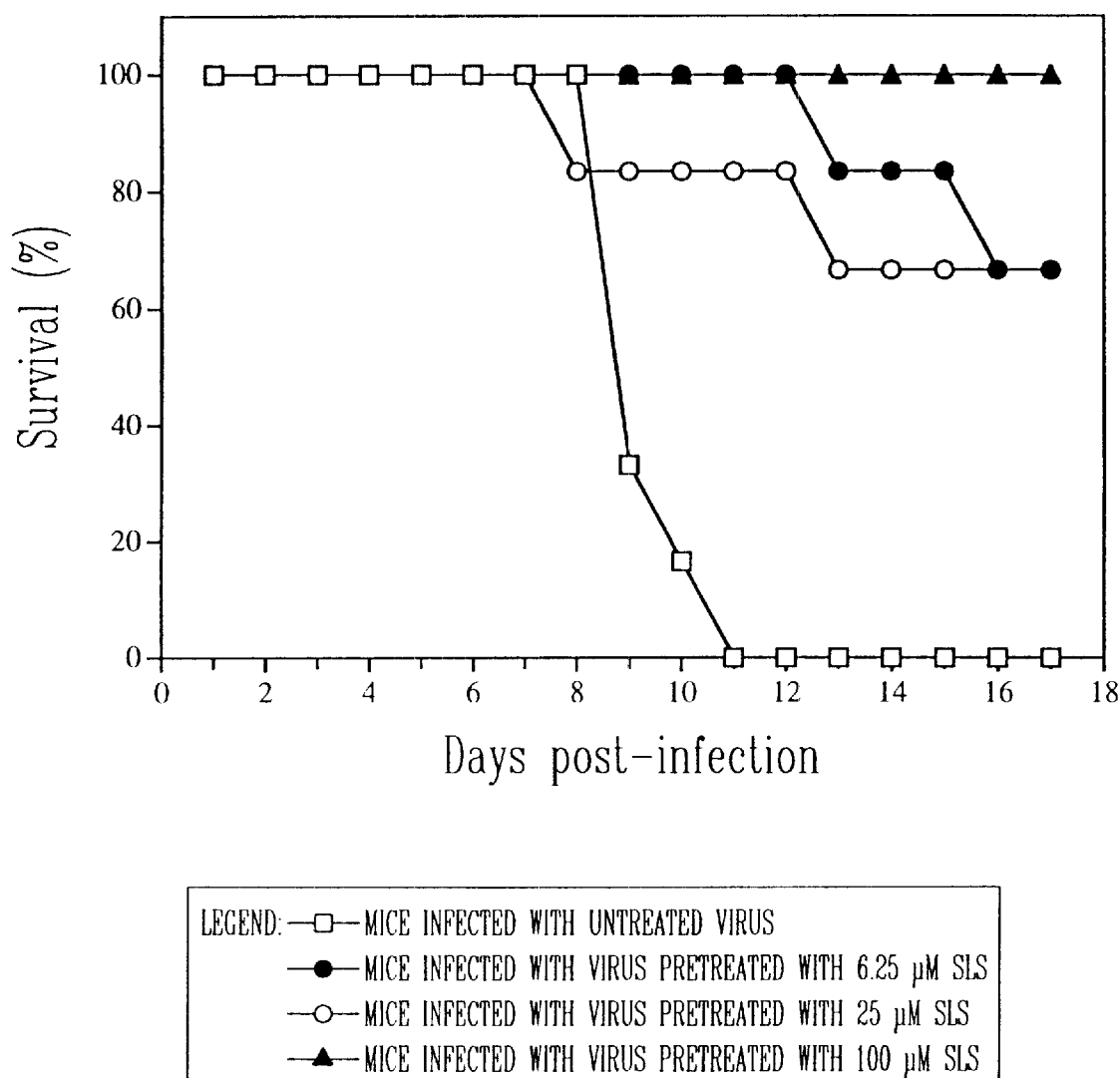

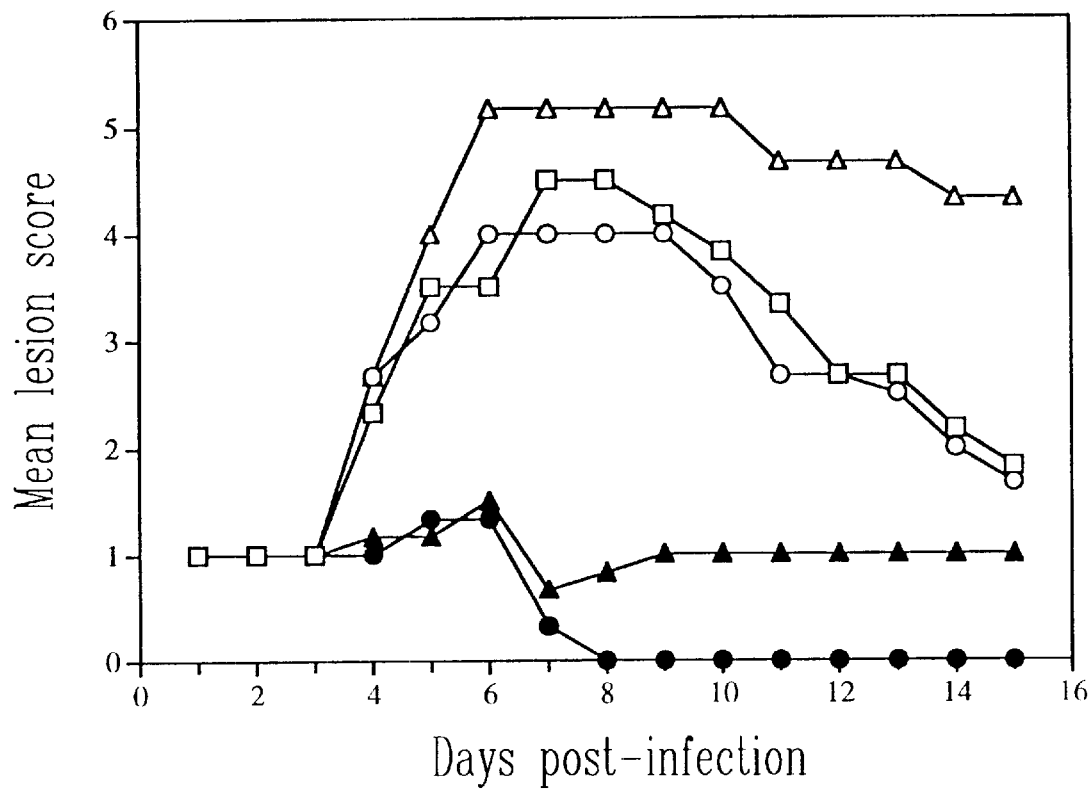

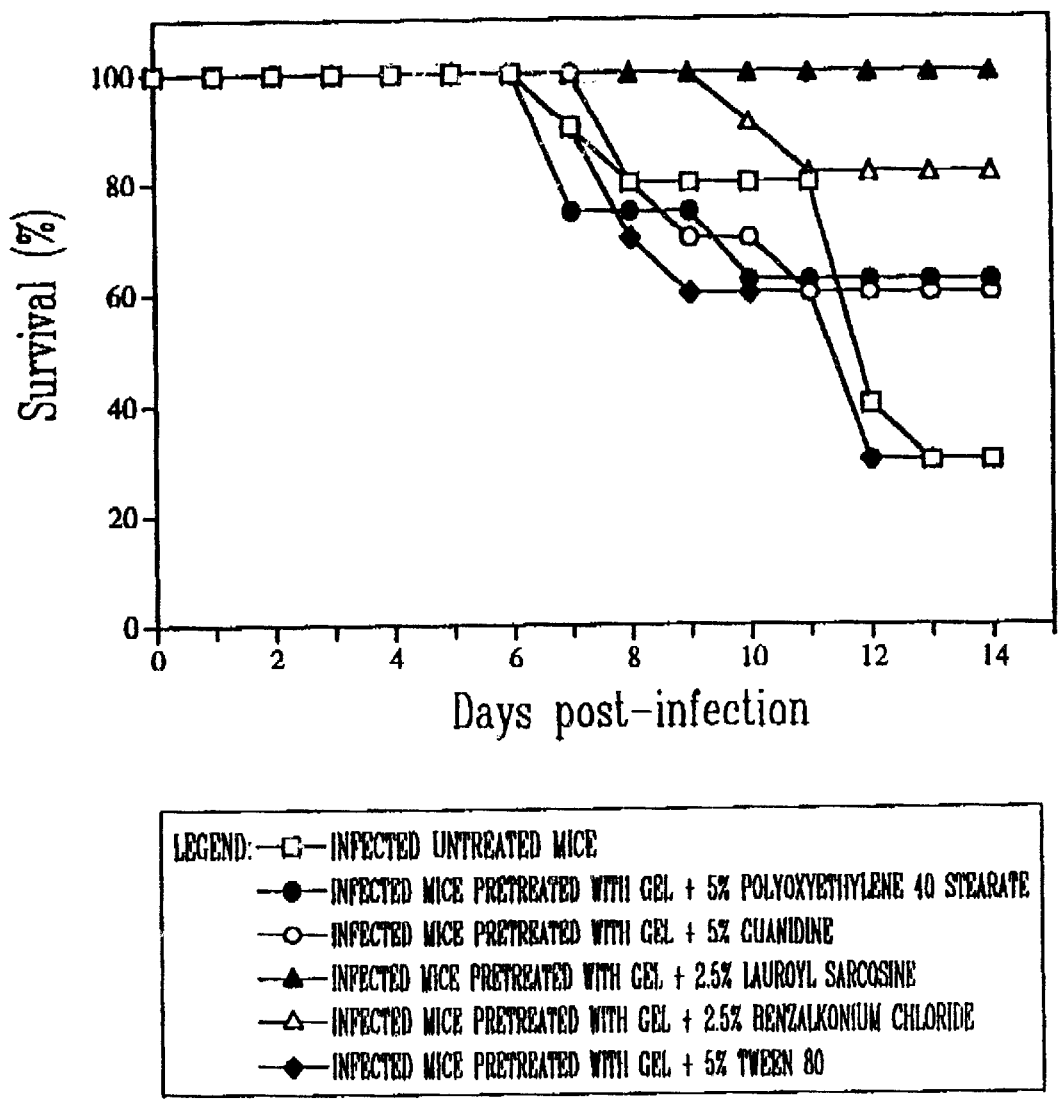

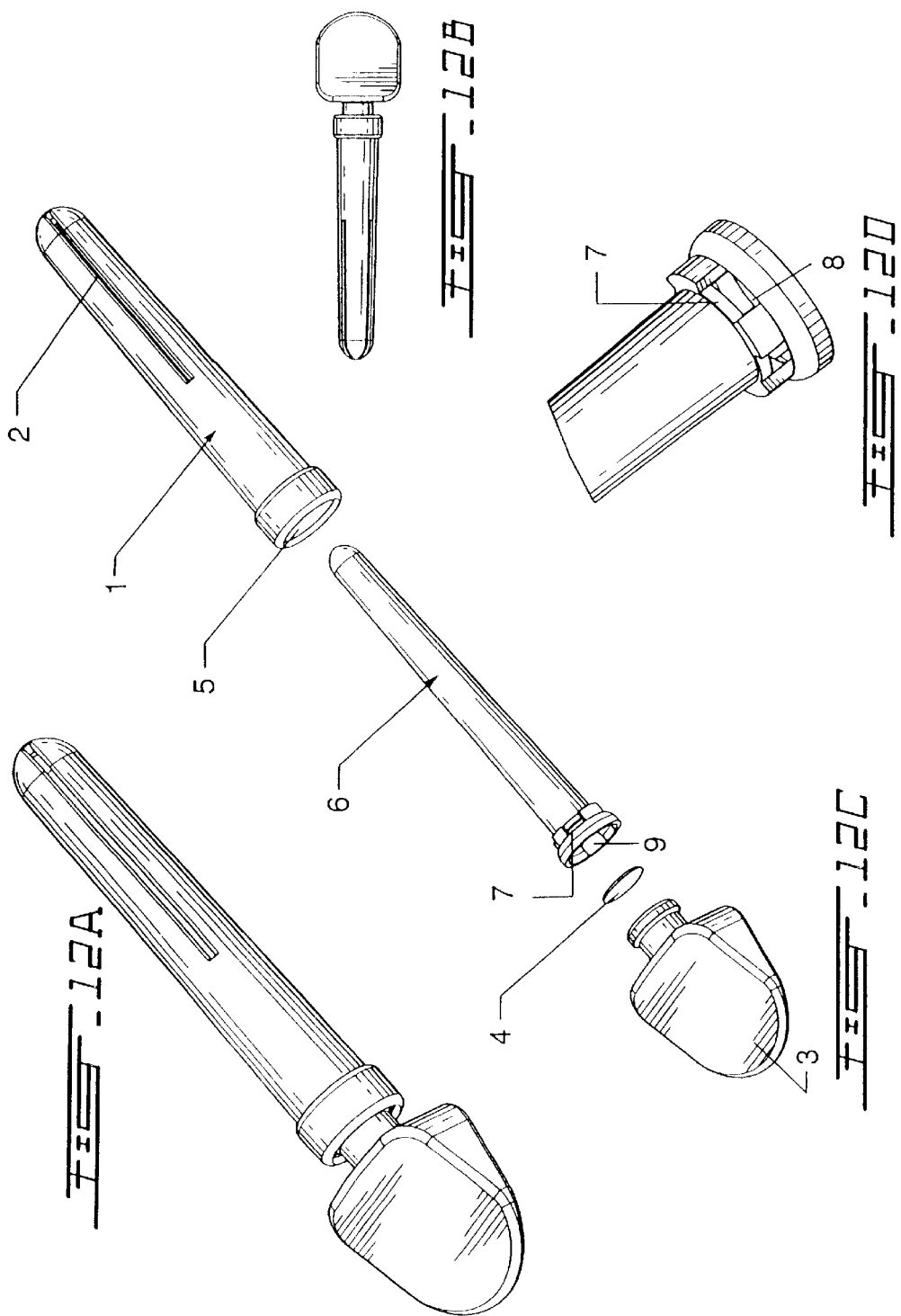

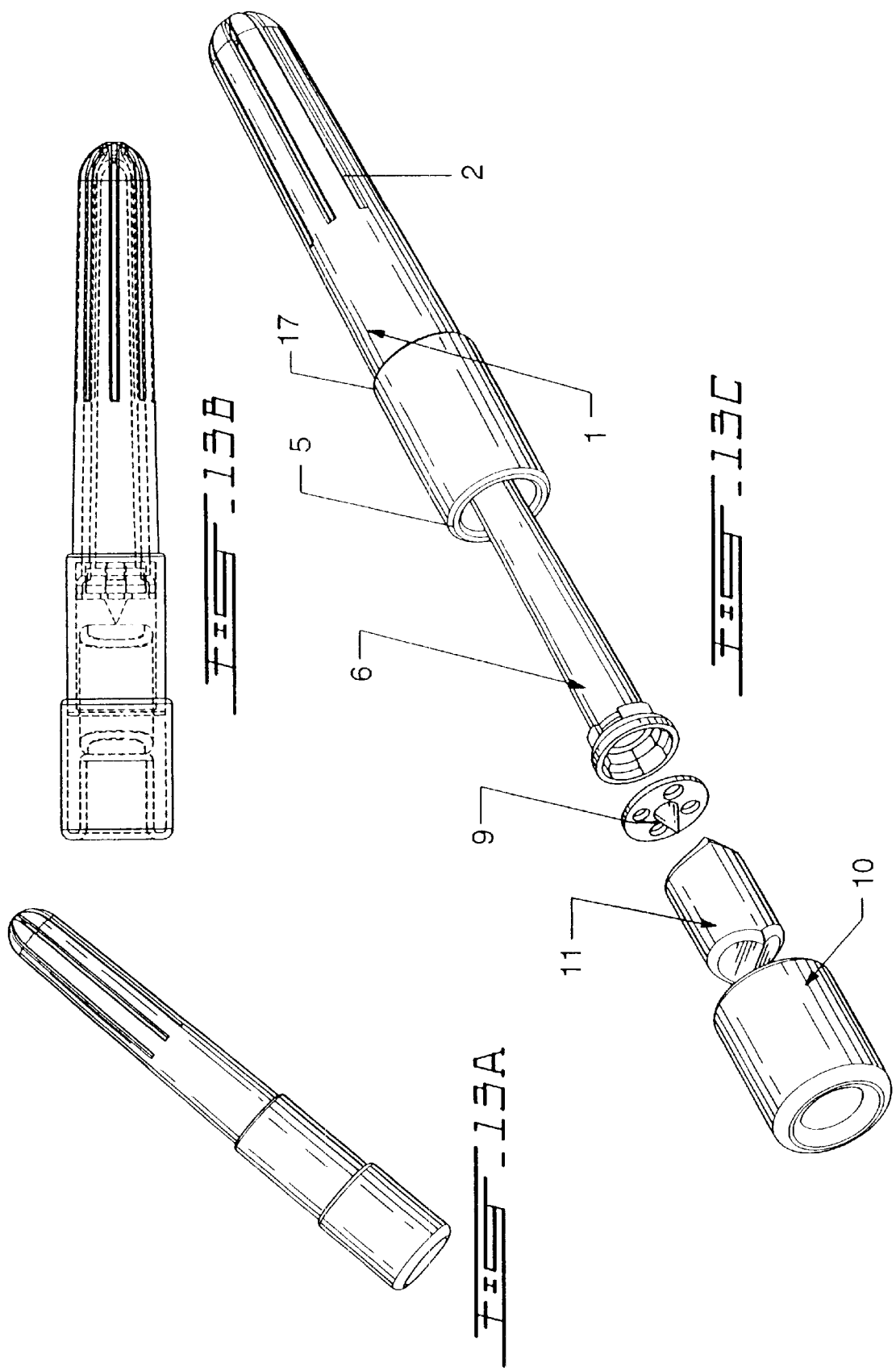

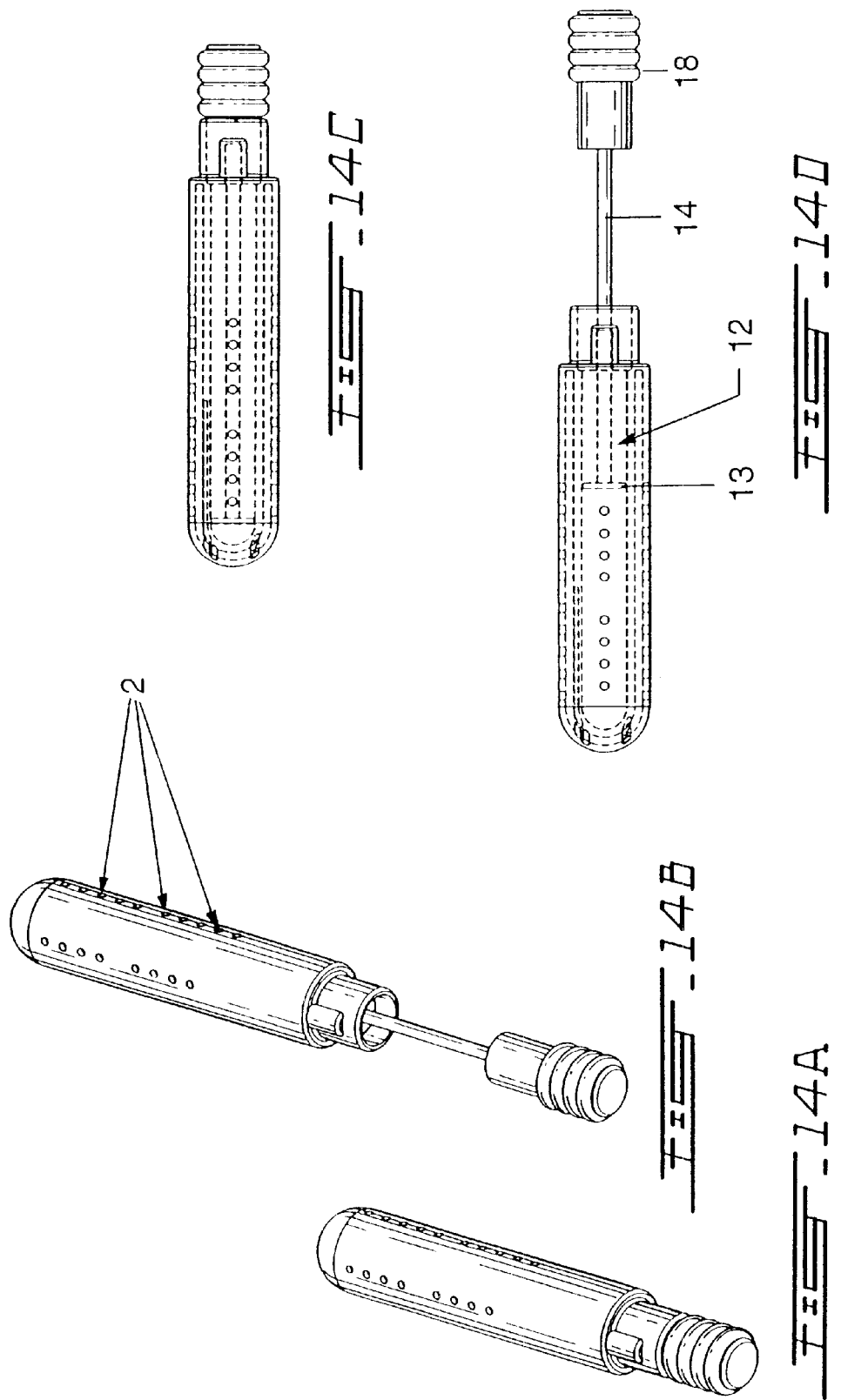

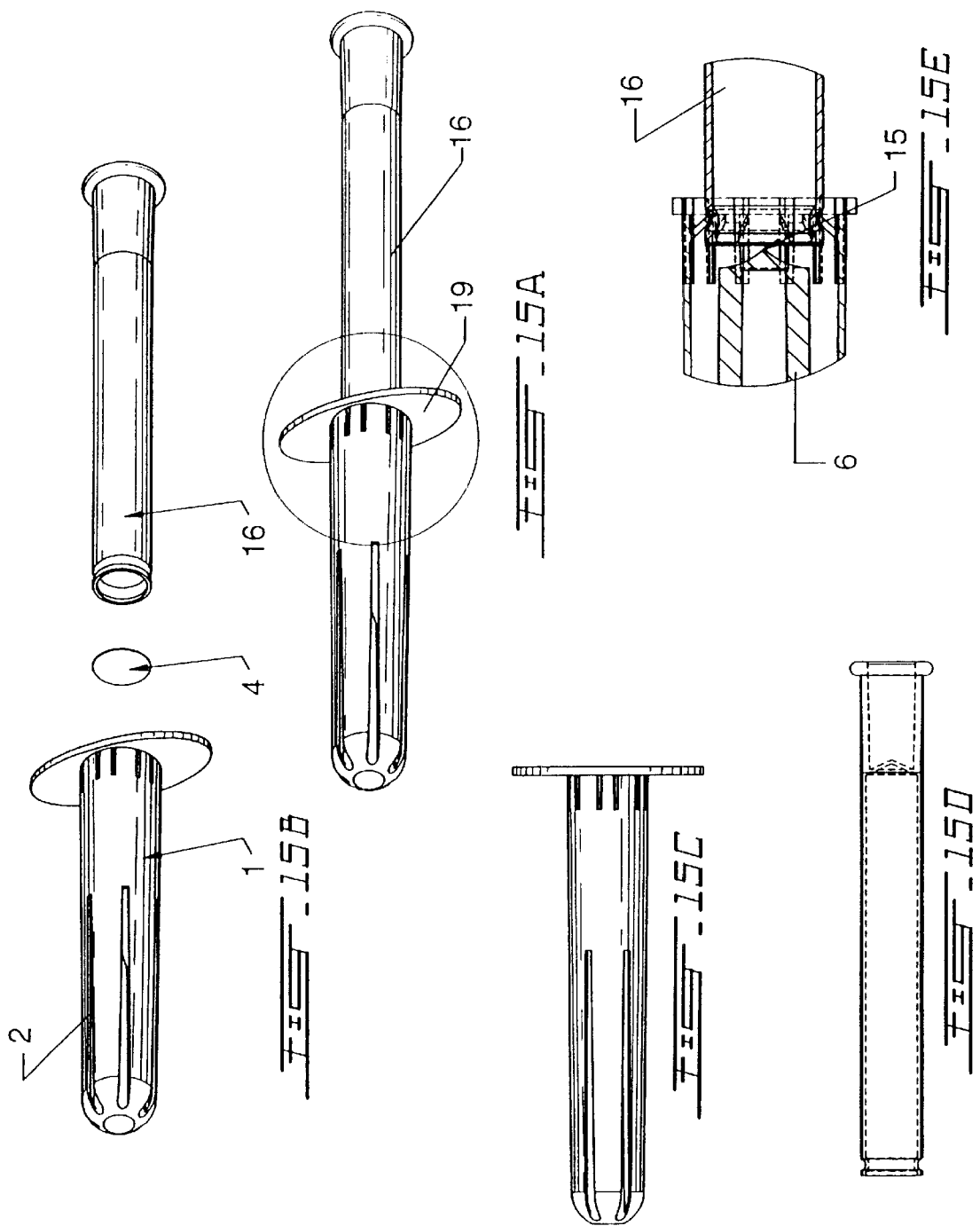

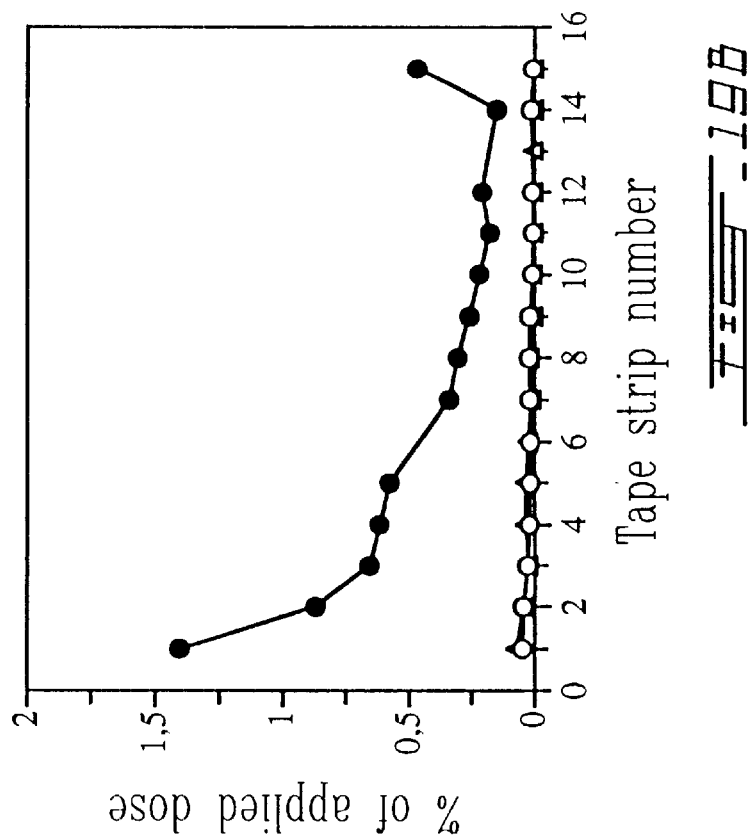
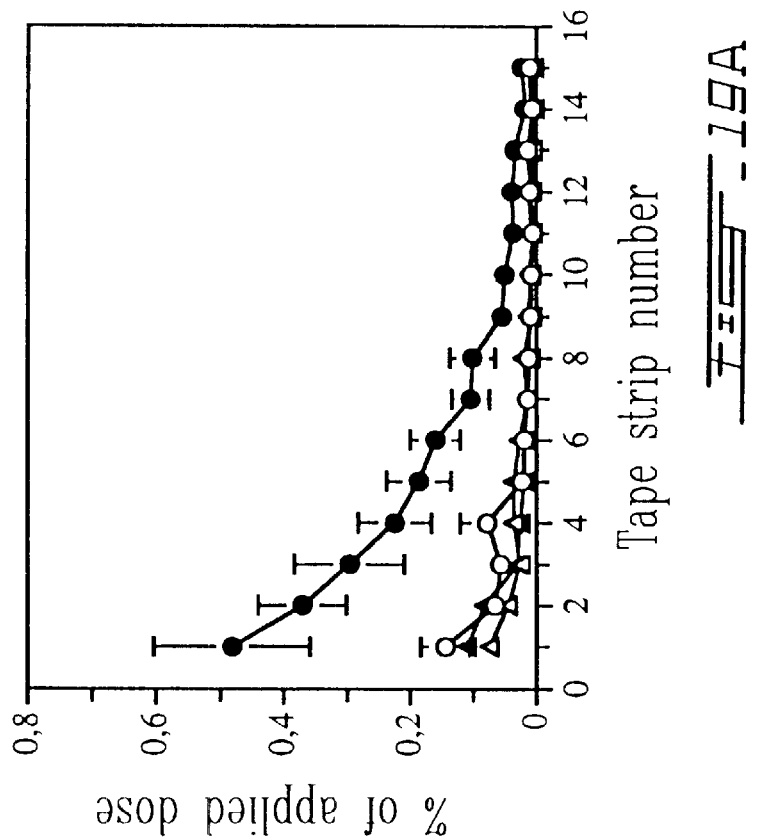
FIG_-19A
FIG_-19B

FORMULATIONS FOR THE PREVENTION OR THE TREATMENT OF DISEASES AFFECTING MUCOSAE OR SKIN, OR FOR PREGNANCY PREVENTION, AND AN APPLICATOR FOR THE DELIVERY OF TOPICAL FORMULATIONS INTO MUCOSAL CAVITIES

This application is a continuation of PCT/CA99/00359 file Apr. 1, 1999.

FIELD OF THE INVENTION

This invention relates to formulations comprising film-forming components and any active ingredient, particularly to topical formulations. More particularly, this invention relates to topical formulations to prevent or to treat diseases associated with or transmitted through mucosae or skin, caused by any causative agent, particularly a pathogen. This invention also relates to an applicator for the uniform delivery of topical formulations to prevent or to treat any disease associated with or transmitted through mucosal cavity, or to prevent invasion by an external agent such as sperm or microbe.

BACKGROUND OF THE INVENTION

The spread of sexually transmitted diseases (STDs) caused by human immunodeficiency virus (HIV), herpes and other pathogens is going at a bewildering rhythm. The global incidence, morbidity, and mortality of STDs are very significant. Worldwide, it is estimated that over 900 million individuals are infected with sexually transmitted pathogens. Each year more than 12 million people in the United States are newly infected with a pathogen responsible for STDs. Herpes simplex virus type-1 (HSV-1) and type-2 (HSV-2), are the most common causes of genital ulceration in developed countries. Genital herpes infection is lifelong and may result in painful and recurrent genital lesions, systemic complications, psychosocial morbidity and also serious neonatal disease following intrapartum transmission of HSV. The genital transmission of this pathogen is usually due to asymptomatic viral shedding by people who are unaware that they are infected. HSV-2 is now detectable in 1 out of 5 americans 12 years of age or older. In addition, it is estimated that over one-third of the world's population has recurrent HSV infections and has therefore the capability to transmit the virus during episodes of productive infection. *Neisseria gonorrheae* and *Chlamydia trachomatis* are recognized as two of the most prevalent sexually transmitted bacterial infections. Worldwide, there is an estimated annual incidence of 25 million cases of gonorrhea and 50 million cases of chlamydia. On the other hand, recent epidemiologic data indicate that the number of individuals infected with HIV is growing dramatically throughout the world. According to United Nations officials, epidemiologic data estimates suggest that as many as 16,000 individuals become infected with HIV every day during 1997. Recent statistics (as of end 1997) from the World Health Organization (WHO) indicated that there are about 31 million people infected with HIV worldwide and this number is projected to reach 40 millions by year 2000.

Globally, heterosexual transmissions may account for 85–90% of HIV infection. As there is no vaccine against HIV, preventive measures are the only tools that can presently reduce the transmission of this retrovirus. The consistent and careful use of condoms represents an effective barrier against the sexual transmission of HIV and other sexually transmitted pathogens, but they should be used in all risky sexual intercourses to significantly reduce the probability of acquiring infection. In Africa, the most intensive prevention programs were only able to increase condom use to approximately 70% of all sexual intercourses in female prostitutes. Consequently, doubts arise about the possibilities of condom promotion in controlling the AIDS epidemic in high risk groups. In situations where heterosexual transmission of HIV is important, preventive measures where women could prevent their risk of contracting STDs could be an additional tool to restrain the epidemic. Such a protective tool may also be used in male homosexual relations as it could provide additional protection under the control of the receptive partner. Therefore, it is important to develop barrier method that could be used as an alternative to condoms where the person could protect themselves against infection without having to ask their sexual partners. Preventive measures aimed at blocking the initial transmission of pathogens that are the causative agents of AIDS, herpes and other STDs will lead, of course, to enormous benefits.

The development of safe topical microbicides is actually a very high priority for the World Health Organization (WHO) and the National Institutes of Health (NIH) in the field of HIV prevention. A topical microbicide is often composed of an active ingredient and a vehicle. Active ingredients may act via a variety of mechanisms including: i) disrupting the organism cell membrane, envelope or capside lipid or protein constituents (e.g. detergent-type spermicides/microbicides such as nonoxynol-9), ii) blocking the receptor-ligand interactions essential for infectivity (e.g. microbial adhesion inhibitors such as sulfated compounds), iii) inhibiting the intracellular or extracellular replication of the pathogen (e.g. antimicrobial drugs), iv) altering the vaginal environment and reducing susceptibility to infection (e.g. buffering agents and products that maintain normal vaginal flora and environment) or v) enhancing local immune responses (e.g. immune response modifiers). The overall efficacy of a topical microbicide against the sexual transmission of pathogens causing STDs depends on the efficacy of the active ingredient to be delivered and its ability to cover the entire vaginal/cervix area for maximal efficacy against pathogens. The capacity of these active agents to cover the entire vaginal cavity greatly depends of the type of vehicle used. Typical formulations of vehicles include gels, creams, foams, suppositories, sponges and films.

Most currently available vaginal formulations use the spermicide nonoxynol-9, a nonionic surfactant, as a microbicide. In vitro, nonoxynol-9 inactivates enveloped viruses, such as HSV, HIV and other microorganisms including *Chlamydia trachomatis, Neisseria gonorrhoeae*. However, the potential efficacy of nonoxynol-9 against HIV is not yet clearly established and results of clinical trials are controversial. A recent controlled trial conducted among 1292 HIV-negative female sex-workers in Cameroon showed that the use of a vaginal film containing 70 mg nonoxynol-9 did not reduce the rate of new HIV, gonorrhea or chlamydia infection (Roddy et al., 1998, N. Engl. J. Med., 339:504–510). The failure of nonoxynol-9 film in reducing the transmission of infectious agents could be attributed to the incomplete coverage of the entire vagina/cervix area with the drug delivery system for nonoxynol-9 or to the occurrence of mucosal toxicity favoring infection of microorganisms. Because of the dramatic increase in the number of individuals throughout the world who are infected with HIV, herpes, or other sexually transmitted pathogens, there is an urgent need to develop active products and/or appropriate delivery systems that can reduce the sexual transmission of these pathogens with minimal mucosal irritation and minimal effects on the vaginal flora and pH.

Sodium lauryl sulfate (SLS) is a sulfated surfactant that denatures membrane proteins of pathogens. It thus has a dual action as a detergent and as a chaotropic agent. With this notion, we have performed experiments to evaluate the potential microbicidal effect of SLS on HSV and HIV. Our preliminary studies clearly demonstrated that SLS modifies in vitro the infectivities of both viruses. More recently, Howett et al. have confirmed our findings that SLS is also a potent inactivator of HSV-2, HIV-1 (Antimicrob. Agents Chemother. 43(2): 314–321, 1999). In addition, they have shown that SLS is effective against rabbit, bovine and human papillomaviruses (non-enveloped viruses) after brief treatment with low concentrations of this product. However, this reference does not teach the use of a vehicle to deliver this potential microbicide. The choice of vehicle is very important because it affects the concentration of available drugs, the duration of drug availability and the degree of mucosal coverage by the formulation which are key factors for offering protection against invading pathogens. Another interesting category of candidate microbicides is microbial adhesion inhibitors, such as sulfated compounds, which block the interaction between host cell receptor and microbe. A known example of microbial adhesion inhibitors is dextran sulfate (DS), a polysulfated carbohydrate, which has been shown to inhibit in vitro the infectivities of HIV and herpesviruses.

We have recently developed a gel formulation that could be applied to the vaginal, cervical or ano-rectal mucosae and which could be effective to prevent sexually transmitted pathogens. One paramount characteristic of this gel formulation is its thermoreversible property. The transition from the liquid state at room temperature to the gel state at body temperature is of prime importance because when applied on rough biological surfaces such as the vaginal or ano-rectal epithelia, the gel should penetrate into the smallest irregularities forming a good physical barrier against infectious agents. The gel formulation has the following key characteristics that both FDA and NIH consider important: i) it is colorless, odorless and non-staining, ii) it should cover the whole vagina/cervix because it is applied in liquid state, iii) it is compatible with male latex condom, iv) it resists to elution by aqueous flow, v) it has a pH similar to that of a healthy vagina (pH 4.0–4.5), vi) it maintains the desired Theological properties under extreme heat and cold conditions and vii) it does not affect, in vitro, the normal vaginal flora, especially *Lactobacillus spp.*

Our international publication (WO 97/42962) discloses the use of formulations comprising film-forming components capable of forming per se a physical barrier to pathogens. Thermoreversible gels such as poloxamers are particularly preferred for that use. The film-forming formulations may further comprise microbicides, spermicides or any other drug, which choice is guided by the pathogen, organism or the disease to be inactivated or treated. The formulations are therefore efficient as a physical, and optionally, as a chemical or pharmacological barrier as well as usable as a sustained drug-release system at the locus of administration. These formulations are intended for use in the prevention of sexually transmitted diseases, as well as in the treatment of infections, cancer, inflammation or any disease or state which requires a pharmacological treatment. In addition, this publication teaches that the formulation decreases the toxicity of potent spermicides/microbicides such as nonoxynol-9. However, this publication does not specifically teach the use of SLS as a chemical candidate of choice incorporated into the topical formulations.

HSV-1 and HSV-2 are neurotropic viruses which infect principally the neuroectodermal tissues including the skin, the peripheral nerves and the central nervous system. Mucosal or skin surfaces are the usual sites of primary infection. Recurrent labialis herpes and genital herpes represent the most common clinical manifestations associated with HSV-1 and HSV-2 infections, respectively. Recurrences are spontaneous but are associated with physical or emotional stress, fever, exposure to ultraviolet light, tissue damage and immune suppression. Although it is a mild disease in immunocompetent individuals, HSV infections are troublesome, especially for patients with frequent episodes. Patients compromised by either immune therapy or underlying disease have increased risk to develop HSV infections. Renal and cardiac transplant recipients demonstrated an increased severity of infection. In addition, the outbreak of AIDS has reinforced the severity of HSV clinical disease in immunocompromised hosts.

The current available topical antiviral treatments have only a limited efficacy particularly against symptomatic recurrent herpes. The limited efficacy of these topical formulations on the development of herpetic mucocutaneous lesions may be due to the poor ability of the drugs to penetrate into the skin. The stratum corneum or horny layer constitutes the barrier for the penetration of most substances into the skin. This layer consists of corneocytes embedded in a double-layered lipid matrix composed of cholesterol, free fatty acids and ceramides. Consequently, the use of skin penetration enhancers could represent a convenient strategy to increase the penetration of topical drug formulations into the skin.

SLS is a surfactant which possesses skin penetration enhancer property by increasing the fluidity of epidermal lipids. The skin penetration enhancer property of SLS combined with its ability to modify viral infectivity via its detergent and chaotropic properties could further increase the efficacy of topical drug formulations. Furthermore, because of its chaotropic properties, SLS may have a broader spectrum of activity against sperm, bacteria, fungi and viruses than another simple detergent.

Poloxamers are widely used in numerous pharmaceutical applications and their nontoxic properties make them suitable for sustained drug delivery systems. Poloxamers represent suitable matrices for dermatological applications. Indeed, when applied in liquid form, poloxamers allow a better surface coverage by penetrating into the smallest irregularities of the mucosa and/or skin. In addition, the reticular array formed by these poloxamers may act as a sustained drug release system prolonging drug action.

SUMMARY OF THE INVENTION

In accordance with the present invention, it is a first object to provide formulations which comprise a film-forming component which is applied to the surface of mucosae or skin, preferably in the form of gel, cream or ointment. The gel formulations are to be used for coating different types of mucosae such as vaginal, cervical, ano-rectal, eye, mouth, nose, or skin to prevent infection and/or abnormal conditions of mucosae and/or skin. Furthermore, the gel formulations can be applied topically to the eye for the treatment and/or prevention of infection of ophthalmic conditions. Preferably, a thermoreversible gel is used, which is applied in a liquid form, spreads on the surface and forms a semi-solid coating after it reaches the temperature of this body surface. More preferably, the thermoreversible gel is composed of poloxamer 407. Similar polymers such as poloxamines can also be used. The above formulations also comprise an agent capable of interfering with the organism cell membrane, envelope or capside lipid or protein constituents in a target cell, tissue or microbe. The above combination of the film-forming component and the above agent may provide for formulations with improved efficacy and reduced toxicity.

In a specific embodiment, the agent is capable of interfering with the binding of a microbial outer protein to a host receptor. In a more specific embodiment, the agent is a microbial adhesion inhibitor, or is a detergent or a chaotropic agent capable of disrupting the integrity of said microbial outer protein. In an even a more specific embodiment, the microbial adhesion inhibitor is dextran sulfate; the detergent is selected from the group consisting of sodium lauryl sulfate, benzalkonium chloride, lauroyl sarcosine, polyoxyethylene fatty acyl derivatives and polyoxyethylene sorbitan fatty acyl ester derivatives; and the chaotropic agent is sodium lauryl sulfate or guanidine. In the most specific embodiment, the agent is SLS, the latter being a chemical candidate of choice because of its numerous properties as a detergent and a chaotropic agent and a putative microbial adhesion inhibitor. SLS alone is efficient against microbes. SLS efficacy is further improved when incorporated into the present formulations. Therefore, it is contemplated that SLS or any equivalent product can be used alone or in combination with the above film-forming component to prevent microbial infection. SLS may be used alone or in combination with the above formulations at any suitable concentration, preferably at a concentration of about 0.1–25% (w/v), and more preferably at a concentration of about 1–15% (w/v). Poloxamer 407 concentration may be used at any suitable concentration, preferably at a concentration of about 5–50% (w/v) and more preferably at a concentration of about 15–35% (w/v) The physical properties of the final formulations largely depends on the drug to be incorporated in them, on the pH and solutes used in the making of the formulations and on the viscosity sought for a given purpose. The above formulations could further comprise a drug which is effective to prevent infection and/or abnormal conditions of the mucosae or skin. Vaginal formulations constitute a physical and a chemical barrier due to its film-forming and microbial disrupting components. It goes along that, with an activity against infective agents, these formulations may also be effective for preventing pregnancy. SLS will advantageously replace nonoxynol-9 in the formulations. SLS having a broader spectrum of activity against, inter alia, sperm, enveloped and non-enveloped viruses, it is a candidate of choice in the present formulation. The gel could contain a drug which is effective to prevent infection and/or abnormal conditions of mucosae and/or skin. For the purpose of the invention, the term "drug" is intended to cover any antimicrobial, bactericidal, virucidal, chemotherapeutic, antiinflammatory, antineoplastic, immunomodulator or any other agent or combination of them which is effective for the prevention of infection of mucosae and/or skin. The term "drug" also refers to cytokines or antigens that could stimulate an immune response that would protect against infection. The drugs could be incorporated within drug carriers such as gels, liposomes, nanoparticles or cyclodextrins, whose encapsulation result in an improved prevention of infection.

It is further an object of the present invention to provide a unique applicator that can be used vaginally and/or anorectally to deliver topical formulations for treatment and/or prevention of infection and/or abnormal conditions of mucosae. The applicator can be designed in different ways to give the same required characteristics specified under detailed description of the invention. Examples of some different concepts are also discussed under the detailed description which are intended to describe some of the general design possibilities of the applicator, but are in no way intended to limit the scope thereof. It is important to mention that the final shape and appearance of the applicator can differ from the examples given herein.

In other preferred embodiments, the present formulations are used to treat viral diseases and they further comprise as a drug an antiviral agent such as acyclovir or foscarnet, or any other antimicrobial agents, used alone or in combination, at any suitable concentration. In a most preferred embodiment, the formulation is composed of poloxamer 407 and contains foscarnet at a concentration ranging from 0.5 to 5% (w/v). In another most preferred embodiment, the formulation is composed of poloxamer 407 and contains acyclovir at a concentration ranging from 0.5 to 5% (w/v). In still another most preferred embodiment, the formulation is composed of poloxamer 407 and contains SLS at a concentration ranging from 1 to 10% and foscarnet or acyclovir at the above concentrations.

It is an object of the present invention to develop new topical formulations to prevent infection of mucosae and/or skin, more particularly those sexually transmitted infections and even more particularly those caused by HIV and herpes. The microbicides or any other drug can be entrapped into the gel formulations either as free or encapsulated into drug carriers such as liposomes, nanoparticles or cyclodextrins. Such microbicidal gels could prolong the local microbicidal activity, eliminate local irritation and reduce systemic side effects of incorporated active agents.

It is also an objective of the invention to develop, for vaginal applications, a unique applicator which allows uniform distribution of the content to the entire vagina (delivery to sides) and cervix (delivery to front) for maximal protection against the sexual transmission of pathogens. Therefore, we have designed a unique applicator which allows about 360° distribution of its content into the vagina and far to the cervix which is a great improvement over existing conventional vaginal applicators which deliver contents only to front (cervix area only).

It is another object of the present invention to develop topical formulations of drugs which could improve the efficacy of chemically or pharmacologically active agents against mucocutaneous infections and more particularly those caused by HSV infections. The improved efficacy of drugs upon incorporation within suitable matrices and/or drug carriers could reduce the dosing interval and consequently improve the quality of life of patients. It is also an objective of the present invention to develop topical formulations for the treatment and/or healing of burn wounds as well as to prevent their potential infection.

DESCRIPTION OF THE SPECIFIC EMBODIMENTS OF THE PRESENT INVENTION

This invention will be described hereinbelow by referring to specific embodiments and appended figures, which purpose is to illustrate the invention rather than to limit its scope.

BRIEF DESCRIPTION OF THE FIGURES

FIG. 3 illustrates the effect of pretreating HIV-1 (strain NL4–3) with 500 μM of SLS for 1 h at 37° C. on its infectivity to 1G5 cells. Values represent the mean±SD of 3 determinations.

FIG. 6 shows the time evolution of survival of mice infected intranasally with HSV-2 (strain 22) pretreated for 1 h at 37° C. with 6.25 (●), 25 (○) and 100 (▼) μM of SLS. Mice infected with untreated virus were used as control (□). Results are expressed as mean of 8 animals per group.

FIG. 8 shows the time evolution of mean lesion score of mice infected with HSV-1 (strain F) following pretreatment of mice with the poloxamer formulation alone 5 min (○) or 1 h (△) prior to infection or with the poloxamer formulation containing 5% SLS also 5 min (●) or 1 h (▼) prior to infection. Infected untreated mice were used as control (□). Results are expressed as mean of 6 animals per group.

FIG. 11 shows the time evolution of survival of mice infected intravaginally with HSV-2 (strain 333) pretreated with gel+5% polyoxyethylene 40 stearate (●), gel+5% guanidine (○), gel+2.5% lauroyl sarcosine (▼), gel+2.5% benzalkonium chloride (△) or gel+5% tween 80 (♦) 5 min prior to infection. Infected untreated mice were used as control (□). Results are mean of 7 to 10 animals per group.

FIG. 12a is a perspective view illustrating a first embodiment of an applicator according to an aspect of the present invention.

FIG. 12b is a side elevational view showing the dimensions in inches of the applicator of FIG. 12a.

FIG. 12c is an exploded view of the components of the applicator of FIG. 12a.

FIG. 12d is a perspective view illustrating the details of the external surface of the proximal end of the internal wall of the applicator of FIG. 12a.

FIG. 13a is a perspective view illustrating a second embodiment of an applicator according to an aspect of the present invention.

FIG. 13b is a side elevational view illustrating the dimensions in inches of the applicator of FIG. 13a in both insertion position and actuated position.

FIG. 13c is an exploded view of the applicator of FIG. 13a.

FIG. 14a is a perspective view of a third embodiment of an applicator according to an aspect of the present invention; the applicator being shown in an insertion position.

FIG. 14b is a perspective view of the applicator of FIG. 14a shown in an actuated position.

FIG. 14c is a side elevational view illustrating the internal details of the applicator of FIG. 14a in the insertion position.

FIG. 14d is a side elevational view illustrating the internal details of the applicator of FIG. 14a in the actuated position.

FIG. 15a is a perspective view of a fourth embodiment of the applicator according to an aspect of the present invention.

FIG. 15b is an exploded view of the applicator of FIG. 15a.

FIG. 15c is a side elevational view of the external wall of the applicator of FIG. 15a where the dimensions are given in inches.

FIG. 15d is a side elevational view of the piston/reservoir of the applicator of FIG. 15a where the dimensions are given in inches.

FIG. 15e is a sectional side elevational view of a portion of the applicator of FIG. 15a illustrating the details of the arrangement of the piston/reservoir with regard to the internal and external walls of the body of the applicator.

Gel Formulations

Figure 1A:
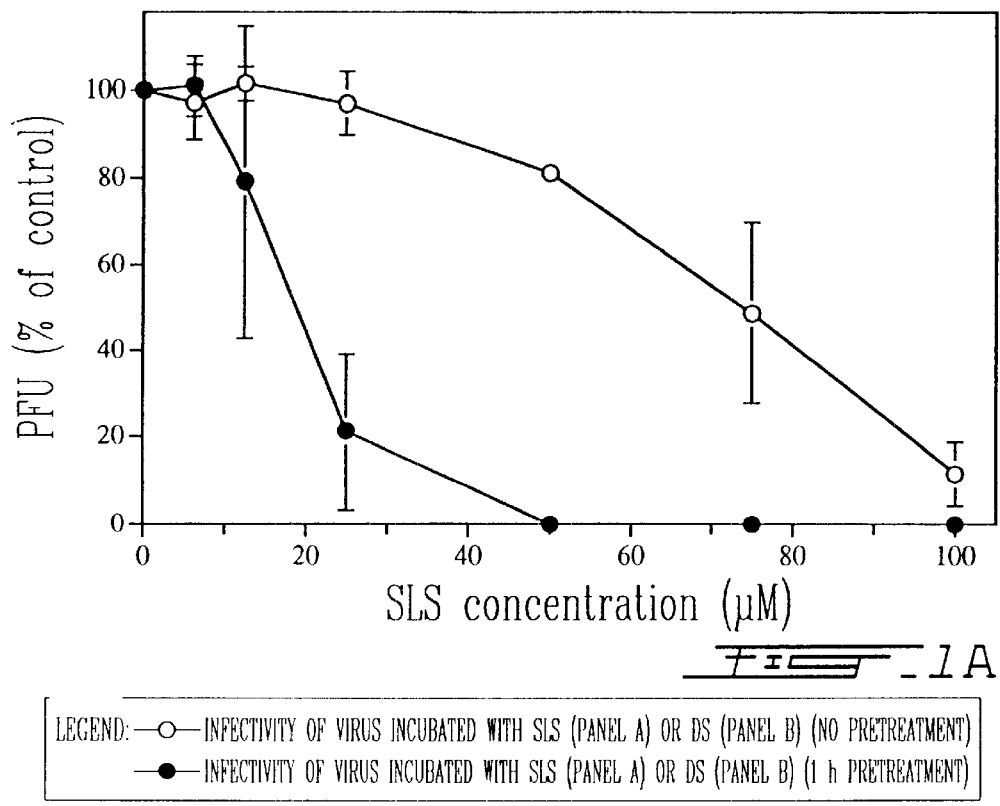
FIG. 1 shows the infectivity of HSV-1 (strain F) to Vero cells following pretreatment of the virus with different concentrations of SLS (Panel A) or DS (Panel B) for 1 h at 37° C. (●) or following the addition of SLS or DS to viruses without pretreatment (○). Plaque forming units (PFU) are expressed as percentage of control. Results are mean±SD of 4 independent experiments.

Poloxamer 407 is a block copolymer of polyoxyethylene and polyoxypropylene in a 7:3 weight ratio with an average molecular weight of 12500. One important characteristic of this block copolymer is its ability to form a thermoreversible gel. The transition from the liquid state at low temperature to the gel state at body temperature (the phase transition temperature being dependent, in part, on the concentration of the gel, the ionic strength and the incorporated solute) allows a number of interesting medical applications including topical applications. Such characteristic is of prime importance because when applied topically in its fluid state to the mucosa, the gel formulation should allow better penetration into the irregularities of the skin and/or mucosae during application and a longer persistence once the gel has reached body temperature. Because of the extremely low toxicity and irritancy of our gel formulations, they represent an attractive approach for topical drug delivery systems. Details for the preparation of the gel formulations are provided hereafter. This invention covers gel formulations of poloxamer 407 of any suitable concentration, and more particularly those between about 10 and 35% w/w. This invention also covers any other film-forming component, gel, cream, ointment or thermoreversible substance including other poloxamers, poloxamines or chemicals.

Drugs

Any antimicrobial, bactericidal, virucidal, chemotherapeutic, antiinflammatory, antineoplastic, immunomodulator or combination of them which is effective to prevent or treat infection and/or abnormal conditions of mucosae and/or skin caused by any pathogen and/or any disease is under the scope of this invention. Any detergent which can disrupt the membrane of pathogens, any skin penetration enhancer that increases the penetration of drugs and/or drug carriers into the mucosae and/or skin, any microbial adsorption inhibitor which prevents pathogen's entry into a target cell, any cytokine or antigen that could stimulate an immune response that would protect against pathogen's infection are also under the scope of this invention. This invention also covers any combination of topical formulations and/or drugs.

Examples Involving our: Gel Gormulations for Prevention of Infection

The following examples are intended to demonstrate the preparation of gel formulations that could be efficient to prevent infection and/or abnormal conditions of mucosae and/or skin caused by any pathogen and/or any disease, but are in no way intended to limit the scope of the present invention.

Preparation of the Gel Formulations

The gel formulations are prepared by adding an appropriate volume of distilled water, buffer or any other suitable aqueous solution to the poloxamer 407 to obtain the desired concentration. An appropriate amount of drugs are then added either to the powder or solution of poloxamer to reach the desired concentration. The pH of the gel formulation can be adjusted to meet the requirements of each target tissue to be coated with the present formulations. For instance, if a formulation is to be used to coat vaginal mucosa, an acidic solution with pH of about 4.0–4.5 will be used. The percentage of polymer may be adjusted accordingly to obtain an adequate transition temperature from liquid to solid state. These adjustments are well within the knowledge and ability of the skilled artisan.

Even though the description of this invention is limited to specific cases, any film-forming component and/or drug and/or liposomes (or other drug carriers) or any combination of the above are considered as potential candidates for the development of these topical presentations and are under the scope of this invention. The formulations also include any film-forming component and/or drug and/or liposomes (or other drug carriers) or any combination of these products at any suitable concentration.

In Vitro Infectivity of Herpes Viruses Pretreated with SLS or DS

The effect of pretreating different strains of herpes viruses with SLS or DS on their viral infectivities to susceptible cells has been evaluated. In brief, cells were seeded in 24 well-plates (Costar, Montreal, QC, Canada). Prior to infection, the virus was either suspended in culture medium or phosphate buffered saline (PBS), or incubated with different concentrations of SLS in PBS for 1 h at 37° C. At confluency, cells were incubated with viral suspensions by centrifuging the plates (750×g for 45 min at 20° C.) to allow virus adsorption. Virus was removed and cell sheets were then overlaid with 0.5 ml of 0.6% agarose Seaplaque (Marine Colloids, Rockland, Mass.) prepared in appropriate culture medium. The plates were incubated for 2 days at 37° C. Cells were then fixed with 10% formaldehyde in PBS for 20 min, washed with deionized water and stained with 0.05% methylene blue. Viral infectivity was evaluated via the determination of Plaque Forming Units (PFU).

Table 1 shows that pretreatment of various HSV-1 and HSV-2 strains with SLS for 1 h at 37° C. decreased, in a concentration-dependent manner, their infectivity on Vero cells. HSV-1 (strain F) infectivity was reduced to 21% when viral particles were pretreated with 25 $\mu$M SLS. The infectivities of all HSV-2 strains were between 50 to 70% following preincubation with 25 $\mu$M SLS. A complete loss of the infectivity of all strains tested were obtained following pretreatment of the viruses with 50 $\mu$M SLS. Preincubation of Vero cells for 1 h at 37° C. with SLS concentrations ranging from 6.25 to 100 μM prior to their infection with HSV-1 (strain F) did not result in a loss of infectivity of the virus (data not shown). These results suggest that SLS acts directly on the virus and not on cells.

harbors two stably integrated constructs made up of the luciferase gene under the control of the HIV-$1_{SF2}$ LTR, has been also evaluated. In brief, prior to infection, the virus was incubated with either culture medium or 500 μM SLS for 1 h at 37° C. Cells ($1 \times 10^5$ cells/well) were then incubated with

TABLE 1

Infectivity of various HSV-1 and HSV-2 strains pretreated with different concentrations of SLS for 1 hour at 37° C.

| SLS concentration (μM) | PFU (% of control) for | | | | |
|---|---|---|---|---|---|
| | HSV-1 (F)[a] | HSV-2 (333)[a] | HSV-2 (22)[a] | HSV-2 (6)[b] | HSV-2 (15589)[c] |
| 6.25 | 101.1 ± 7.0 | 102.9 ± 23.5 | 128.0 ± 18.5 | 105.3 ± 12.4 | 108.7 ± 22.2 |
| 12.5 | 79.2 ± 36.4 | 115.4 ± 17.0 | 103.4 ± 14.9 | 82.1 ± 40.7 | 115.1 ± 17.5 |
| 25 | 21.2 ± 18.0 | 72.9 ± 9.1 | 63.8 ± 11.9 | 51.1 ± 30.1 | 59.0 ± 24.0 |
| 50 | 0 | 0 | 0 | 0 | 0 |

[a]wild-type strain
[b]acyclovir-resistant strain
[c]foscarnet-resistant strain

Figure 1B:
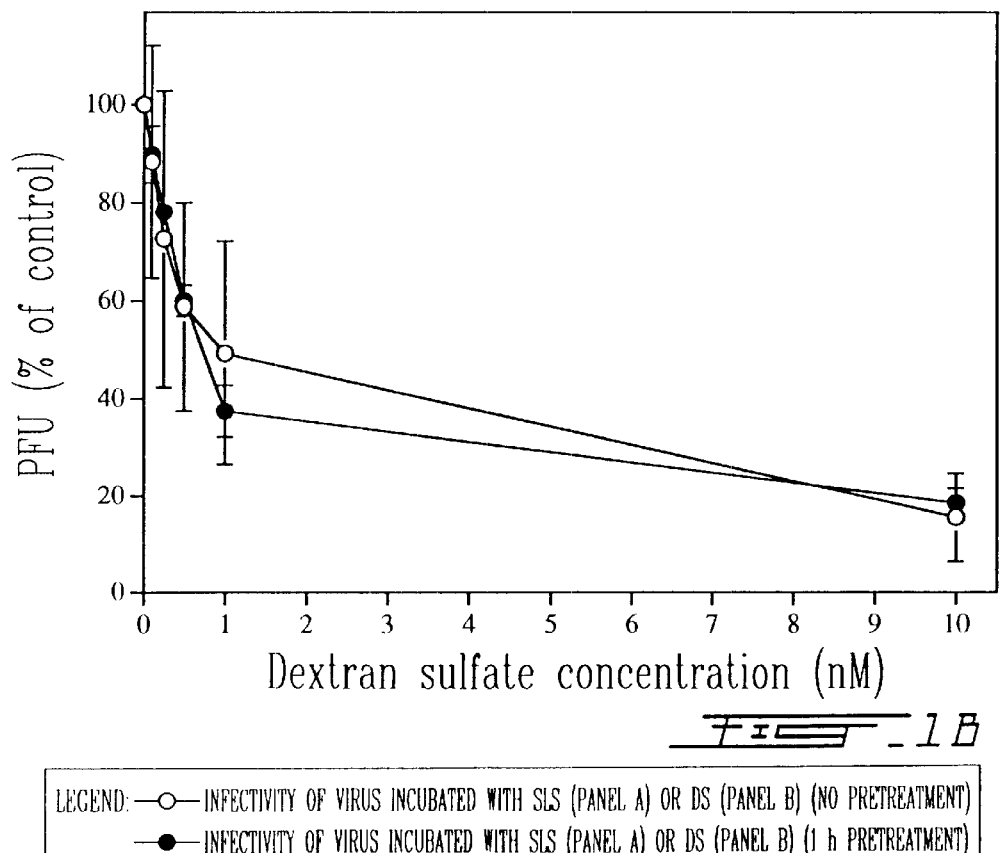

FIG. 1 shows the effect of pretreatment of HSV-1 (strain F) with different concentrations of SLS or DS on its infectivity to Vero cells. When SLS was immediately added to Vero cells following their infection, the loss of viral infectivity was less dramatic compared to that obtained for virus pretreated for 1 h at 37° C. with the same SLS concentrations. Following pretreatment, a loss of 50% of the viral infectivity was observed at a concentration of 20 μM compared to 75 μM when the virus was not pretreated. Moreover, although a complete inhibition of viral infectivity was obtained following preincubation with 50 μM SLS, the inhibition was not complete even at 100 μM without pretreatment. Similarly, pretreatment of the HSV-2 (strain 333) with SLS also influenced the infectivity of this strain (data not shown). On the other hand, DS reduces the infectivity of the virus independent of whether the virus was pretreated with DS. In this case, a loss of 50% of the viral infectivity was observed at a concentration of about 1 nM.

The viability of Vero cells exposed for 1 h at 37° C. to SLS or DS concentrations similar to those used in FIG. 1 and Table 1 was also tested using an MTS test. No signs of cytotoxicity could be demonstrated in the range of concentrations used (data not shown).

Figure 2A:
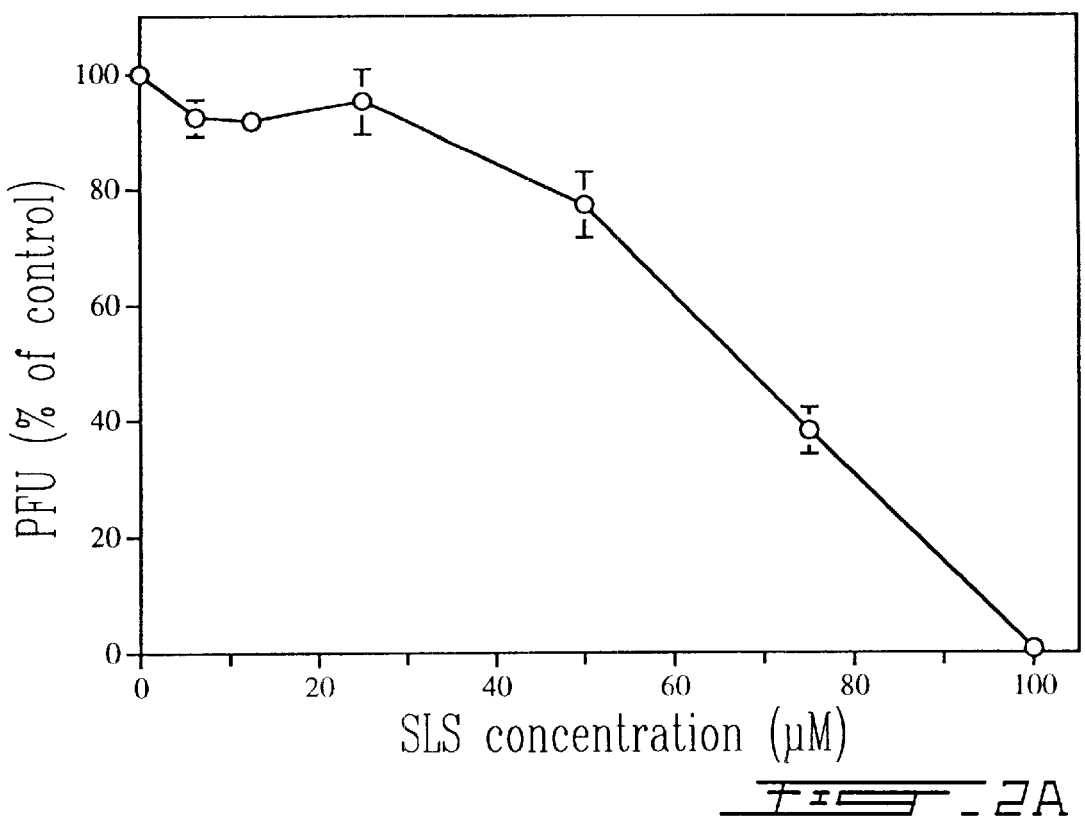
FIG. 2 shows the efficacy of different concentrations of SLS (Panel A) or DS (Panel B) against HSV-1 (strain F) in Vero cells. Plaque forming units (PFU) are expressed as percentage of control. Results are mean±SD of 4 independent experiments.
Figure 2B:
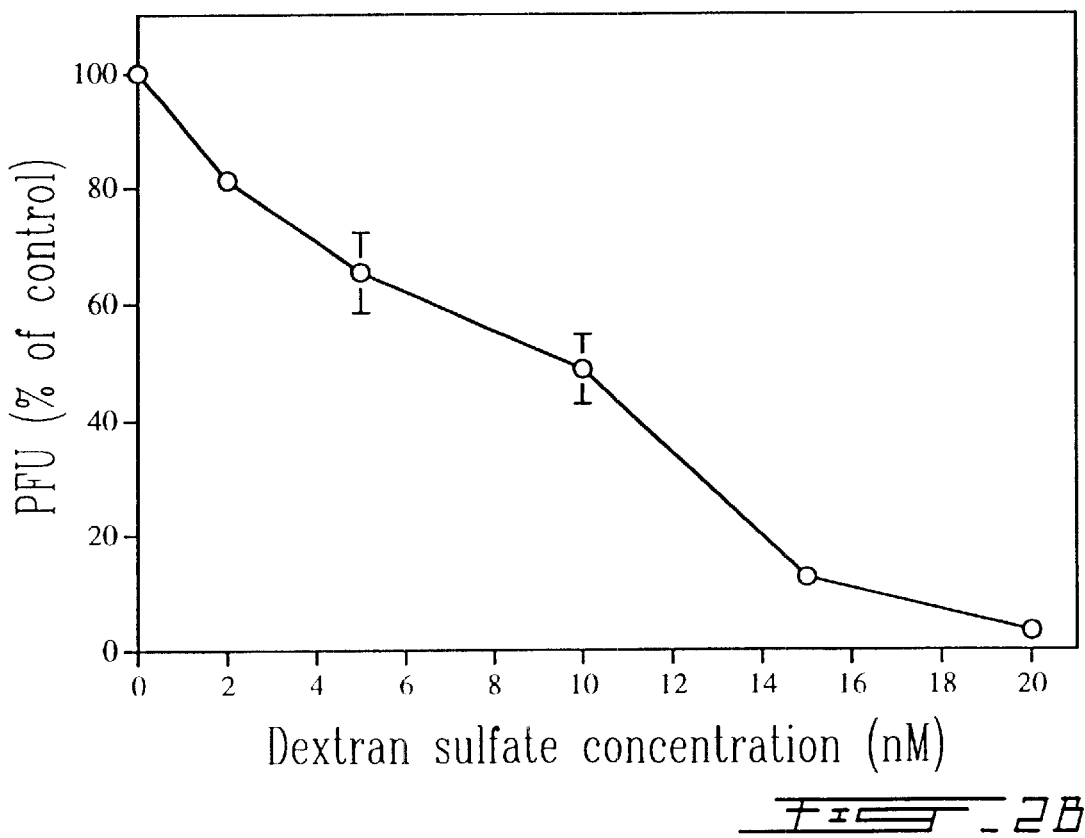
Figure 4A:
FIG. 4 shows electron micrographs of Vero cells infected with HSV-1 (strain F) pretreated for 1 h at 37° C. with 50 μM (Panel B), 75 μM (Panel C) and 100 μM (Panel D) of SLS. Cells infected with HSV-1 (strain F) in absence of SLS were used as control (Panel A). Magnification 70,000×.
Figure 4B:
Figure 4C:
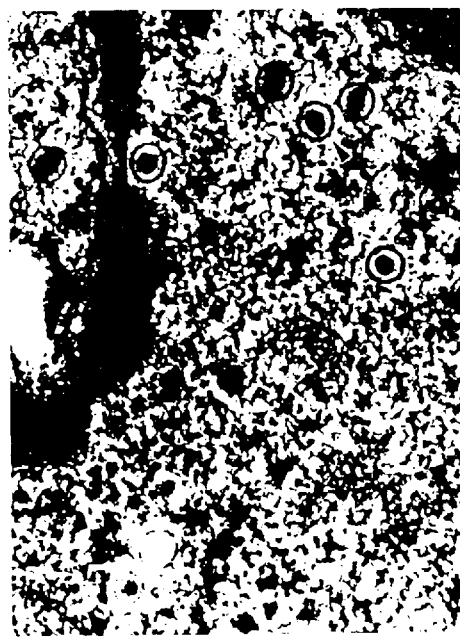
Figure 4D:

FIG. 2 shows the efficacy of different concentrations of SLS (Panel A) or DS (Panel B) against HSV-1 (strain F) in Vero cells. In brief, cells were infected with the virus for 2 h at 37° C. Afterwards, supernatant was removed and cells were overlaid with 0.5 ml of EMEM+2% FBS containing 0.6% agarose Seaplaque and SLS or DS at the desired concentration. Plates were then incubated for 2 days at 37° C. in a 5% $CO_2$ atmosphere. Cells were fixed with 10% formaldehyde in PBS for 20 min, washed with deionized water and stained with 0.05% methylene blue. Viral infectivity was evaluated following the determination of PFU. Results show that both SLS and DS reduced in a concentration-dependent manner the viral repication in a similar way with complete efficacy at 100 μM and 20 nM for SLS and DS, respectively. Without being bound to any mechanism, the above results suggest that SLS may have a microbial adhesion inhibitor effect.

In Vitro Infectivity of HIV-1 Pretreated with SLS

The effect of pretreating HIV-1 (strain NL4-3) with SLS on its infectivity to 1G5 cells, a Jurkat E6-1 derivative that harbors two stably integrated constructs made up of the luciferase gene under the control of the HIV-$1_{SF2}$ LTR, has been also evaluated. In brief, prior to infection, the virus was incubated with either culture medium or 500 μM SLS for 1 h at 37° C. Cells ($1 \times 10^5$ cells/well) were then incubated with HIV-1 strain NL4-3 (10 ng of p24) for 2 h at 37° C. under a 5% $CO_2$ atmosphere. Afterwards, cells were washed, resuspended in 200 μl of complete culture medium and transferred in a 96-well flat-bottomed tissue culture plate (Microtest III, Falcon; Becton Dickinson, Lincoln Park, N.J.). After a 48 h incubation time at 37° C., cells were lysed, subject to a freeze-thaw cycle and luciferase activity was monitored using a microplate luminometer (MLX; Dynex Technologies, Chantilly, Va.). Results from this set of experiments clearly show that pretreatment of HIV-1 (strain NL4-3) with 500 μM SLS for 1 h at 37° C. almost completely inhibited HIV-1 infectivity to 1G5 cells (FIG. 3).

Electron Microscopy of Vero Cells Infected with HSV-1 (Strain F) Pretreated with SLS The appearance of HSV-1 (strain F) pretreated with varying SLS concentrations (50, 75 and 100 μM) for 1 h at 37° C. has been evaluated in Vero cells using electron microscopy. In brief, cells (80–90% confluent) were infected with the virus (approximately 70 PFU/ml in 14 ml) for 48 h at 37° C. in a 5% $CO_2$ atmosphere. Cells were scrapped off from the dishes and resuspended in culture medium. Cells were centrifuged (515×g for 10 min at 4° C.) and the supernatant was decanted and cells were resuspended in approximately 500 μl medium. Cells were transferred in an eppendorf tube and centrifuged at (10,000×g for 5 min at 4° C.). The pellet was resuspended in approximately 200 μl of 20% bovine serum albumin (BSA). Few drops of 25% glutaraldehyde were added to the mixture and samples were immediately put in an ice bath to allow BSA polymerization. The pellet was then cut in 1 $mm^3$ samples which were then fixed in 2% glutaraldehyde in PBS for 1 h, 1% $OsO_4$ in PBS for 1 h and then with 0.1% tannic acid in PBS for 30 min. Samples were rinsed 3 times in PBS for 5 min between each step. Samples were stained with 2% uranyl acetate in 10% ethanol for 30 min. Samples were dehydrated and embedded in Epon following routine procedures. Sections (approximately 75 nm thickness) were mounted on copper grid (200 mesh). Specimens were stained with uranyl acetate, counterstained with lead citrate and observed with a JEOL 1010 electron microscope (JEOL Canada Inc., St-Hubert, QC, Canada).

FIG. 4 (Panel A) shows the normal appearence of the virus in the nuclei of Vero cells. Viral particles were composed of a capsid, hexagonal in shape and, containing an electrondense DNA core. Complete viral particles formed by a nucleocapsid surrounded by an envelope were also found in the cytoplasm of most cells. In Vero cells infected with viruses pretreated with 50 (Panel. B), 75 (Panel C) and 100 (Panel D) $\mu$M SLS, viral particles could be recovered in the nuclei but not in the cytoplasm of cells. No mature nucleocapsid could be observed in the nuclei but viral particles were constituted by capsids containing a discrete accumulation of electron-dense material. The number of empty capsids found in nuclei of cells infected with viruses pretreated with SLS decreased with the increased concentrations of drug used for the pretreatment,. In cells infected with viruses pretreated with 100 $\mu$M SLS, only a few cells with empty capsids in the nuclei could be detected. Taken together, thes results could explain the loss of infectivity of herpes viruses in presence of SLS.

Quantification of HSV 2 Glycoprotein D Gene

The quantification of the glycoprotein D gene of HSV-1 (strain F) pretreated with SLS was also evaluated in Vero cells in order to determine the presence of viral DNA in the infected cells. In brief, HSV-1 (strain F) was pretreated with varying SLS concentrations (12.5, 25, 50, 75 and 100 $\mu$M) in EMEM+2% FBS for 1 h at 37° C. Vero cells (80–90% confluent) were infected with the virus (100 PFU/ml in 20 ml) for 48 h at 37° C. in a 5% $CO_2$ atmosphere. The culture medium was removed and cell sheet was washed twice with 1×HBSS. Cells were scrapped off from the dishes and resuspended in EMEM+2% FBS. Total DNA was extracted using a standard phenol/chloroform procedure. Quantitation of total DNA was achieved using the Burton procedure. The probe used for this study corresponds to a part of glycoprotein D of HSV-2 (strain 333), generated by PCR using the following primers:

P1 (5'-GCCACCATGGGGCGTTTGACC-3') and

P2 (5'-AAACTCAGTTATCTAGTCCTCGGGGTC-3')

and was [$^{32}$P]-labeled by random priming. Hybridization was performed at 65° C. in 0.25 M $Na_2HPO_4$ (pH 6.8 with orthophosphoric acid) and 7% SDS. Washes were done in 40 mM $Na_2HPO_4$ (pH 6.8 with orthophosphoric acid) and 1% SDS for 20 min at 65° C. followed by 20 min at 25° C.

Figures 5A, 5B:
FIG. 5 shows quantification of glycoprotein D of HSV-1 (strain F) pretreated for 1 h at 37° C. with 12.5, 25, 50, 75 and 100 μM of SLS in Vero cells. Cells infected with HSV-1 (strain F) in EMEM +2% FBS were used as control. Values are expressed as a percentage of the hybridization signal intensity compared to control.

FIG. 5 (Panel A) shows the quantification of the glycoprotein D gene of HSV-1 (strain F) pretreated with varying concentrations of SLS in Vero cells. Following a 48 h incubation, cells were collected and total DNA was extracted. Panel A shows BglII-fragmented DNA aliquots (325 ng) applied to a 0.8% agarose gel, transferred to a nylon membrane, and hybridized with the glycoprotein D probe. Panel B shows the quantitative measurements of HSV-1 DNA levels obtained by scanning densitometry of the autoradiogram using an AlphaImager. No major modification in the expression of the glycoprotein D gene of the virus could be observed in cells infected with HSV-1 (strain F) pretreated with 12.5, 25 and 50 $\mu$M SLS compared to control. Quantitative measurements of HSV-1 DNA levels obtained by scanning densitometry of the autoradiogram were similar (Panel B). However, when the virus was pretreated with higher concentrations of SLS (75 and 100 $\mu$M), a marked reduction in the expression of the glycoprotein D gene was observed with a reduction in the DNA levels to 65.1% and 34.9% of control values, respectively. These data suggest that SLS could interfere with the maturation of viral nucleocapsids either by reducing their rate of maturation or by interfering with the encapsidation of DNA into the capsid shell.

In Vivo Infectivity of Herpes Viruses Pretreated with SLS (Intranasal Model)

The effect of pretreating HSV-2 (strain 22) with SLS on viral infectivity has also been evaluated in a murine intranasal infection model. In brief, female Balb/c mice (Charles River Breeding Laboratories Inc., St-Constant, QC, Canada) 4 weeks-old were used throughout this study. Prior to the infection, HSV-2 (strain 22) was incubated for 1 h at 37° C. with PBS or with different concentrations of SLS (6.25, 25 or 100 $\mu$M) to reach a final viral inoculum of 2,000 PFU/20 $\mu$l. Mice were slightly anesthetized using Aerrane® (Isoflurane, USP; Janssen, North York, ON, Canada) and viral suspension (20 $\mu$l total volume) was applied into the external left nare of mice. Mice were then returned to their cages and survival was evaluated daily.

FIG. 6 shows that all mice infected with untreated virus died of encephalitis between day 9 and day 11. In contrast, 67% of mice infected with the viral inoculum pretreated with 6.25 and 25 $\mu$M SLS survived the infection. Of prime interest, all mice infected with a viral suspension pretreated with 100 $\mu$M SLS survived the infection and did not demonstrate any sign of illness.

In Vivo Infectivity of Herpes Viruses Pretreated with SLS or DS (Cutaneous Model)

The effect of pretreating HSV-1 (strain F) with SLS on viral infectivity has also been evaluated in a murine cutaneous infection model. Female hairless mice (SKH1; Charles River Breeding Laboratories Inc., St-Constant, QC, Canada), 5–6 weeks old were used throughout this study. Prior to infection, HSV-1 (strain F) was incubated for 1 h at 37° C. with PBS, with 6.25, 25 or 100 $\mu$M SLS or with 0.25, 1 or 10 nM DS to obtain a viral inoculum of $3 \times 10^5$ PFU/50 $\mu$l. Mice were anesthetized by intraperitoneal injection of a mixture containing 70 mg/kg ketamine hydrochloride (Rogarsetic* injection USP; Rogar/STB Inc. Montreal, QC, Canada) and 11.5 mg/kg xylazine (Rompun®; Miles Canada Inc., Etobicoke, ON, Canada). The virus was inoculated on the lateral side of the body in the left lumbar skin area. The skin was scratched six times in a crossed-hatched pattern with a 27-gauge needle held vertically. Viral suspension (50 $\mu$l) was deposited onto the scarified area and rubbed for 10 to 15 sec with a cotton tipped applicator saturated with EMEM+2% FBS or SLS or DS solutions. The scarified area was protected with a corn cushion which was maintained on the mice body with surgical tape. The porous inner wall of the aperture of the corn cushion was impermeabilized with tissue adhesive prior to use to prevent absorption of the drug. The aperture of the corn cushion was also closed with surgical tape. Mice were then returned to their cages and observed twice daily.

Figure 7A:
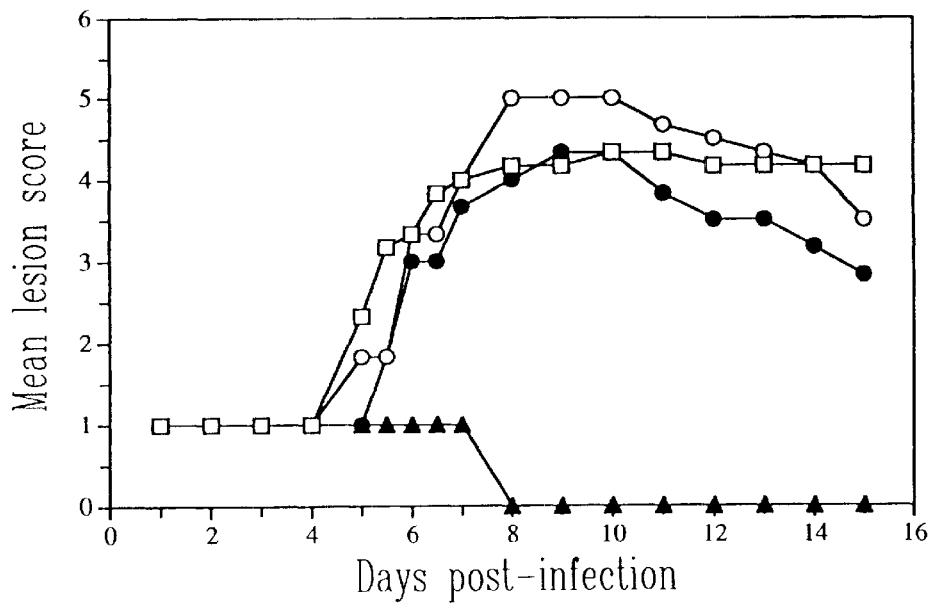
FIG. 7 shows the time evolution of the mean lesion score of mice infected cutaneously with HSV-1 (strain F) pretreated for 1 h at 37° C. with different concentrations (6.25 (●), 25 (○) and 100 (▼) μM) of SLS (Panel A) or different concentrations (0.25 (●), 1 (○) and 10 (▼) nM) of DS (Panel B). Mice infected with untreated virus were used as control (□). Results are expressed as mean of 6 animals per group.
Figure 7B:
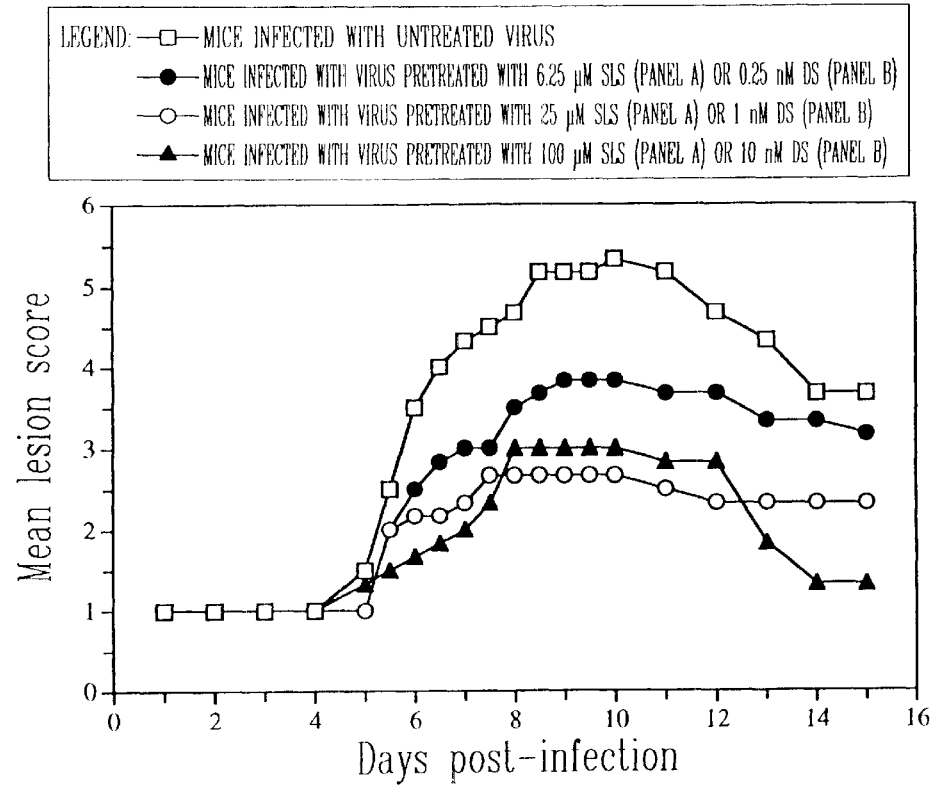

FIG. 7 shows the time evolution of the mean lesion score of hairless mice infected cutaneously with HSV-1 (strain F) pretreated with different concentrations of SLS or DS for 1 h at 37° C. The evaluation of the lesion score was performed according to the criteria presented in Table 2. In infected untreated mice, no pathological signs of cutaneous infection were visible during the first four days following infection and only the scarified area remained appearent. On day 5, herpetic skin lesions began to appear in some mice in the form of small vesicles distant from the inoculation site. On day 6, almost all untreated mice developed herpetic skin lesions in the form of a 4–5 mm wide band extending from the spine to the ventral midline of the infected dermatome similar to zoster-like infections. Maximal mean lesion score was observed on day 8. Mean lesion score decreased thereafter from day 11 to day 15 because of spontaneous regression of cutaneous lesions in some mice. Mice infected with the virus pretreated with 6.25 and 25 $\mu$M SLS did not demonstrate a significant reduction of the mean lesion score. However, mice infected with the virus pretreated with 100

μM SLS did not demonstrate any signs of cutaneous lesions. Of prime importance, all mice infected with the virus pretreated with 100 μM SLS survived the infection (data not shown). On the other hand, mice infected with the virus pretreated with 0.25 nM DS showed a partial reduction of the mean lesion score whereas mice infected with the virus pretreated with either 1 or 10 nM DS gave better protection against the development of herpetic lesions.

TABLE 2

Criteria used for the evaluation of herpetic cutaneous lesions

Score  Appearance of the lesion

0  No visible infection
1  Infection visible only at inoculation site, scarification area
2  Infection at inoculation site only, with swelling, crust and erythema
3  Infection at inoculation site with discrete lesions forming away from inoculation site
4  Rash visible around half of body but not yet confluent
5  Rash confluent but not yet necrotic or ulcerated
6  Complete rash with necrosis or ulceration, hind limb paralysis, bloating, death In Vivo Prophylactic Effect of Poloxamer Formulations Containing or not SLS (Cutaneous Model)

The efficacy of the poloxamer alone and of the poloxamer containing 5% SLS to prevent the development of cutaneous lesions in mice has also been evaluated. Female hairless mice (5–6 weeks old) were used throughout this study. In brief, mice were anesthetized by intraperitoneal injection of a mixture containing 70 mg/kg ketamine hydrochloride and 11.5 mg/kg xylazine. The formulations were applied topically on the lateral side of the body in the left lumbar skin area. Five minutes and 1 hour after the application, one drop of viral inoculum ($3.15 \times 10^8$ PFU/ml) was deposited onto the skin and a scarification was made with a 27G needle throughout the drop to mimic an accident that may occur to health care workers. In this model, the viral inoculum needs to be higher to obtain a complete zosteriform rash in almost all mice. However, the mortality associated to infection was low and could not be used as a criteria to evaluate the efficacy of treatments. The scarified area was protected with a corn cushion which was maintained on the mice body with surgical tape. The aperture of the corn cushion was also closed with surgical tape. Mice were then returned to their cages and observed twice daily.

FIG. 8 shows the time evolution of the mean lesion score of infected untreated mice and of mice pretreated with the poloxamer alone or poloxamer containing 5% SLS 5 min or 1 h prior to their cutaneous infection with HSV-1 (strain F). Results show that mice pretreated with the gel alone 5 min or 1 h prior to infection give only a modest protection against the development of cutaneous lesions. Of prime interest, in mice pretreated both 5 min or 1 h with the poloxamer containing 5% SLS, a complete protection against the development of cutaneous lesions was observed. These results show the great potential of our formulations as a prophylactic approach to prevent infection with pathogens. Such a tool could indeed protect against accidental infection of health care workers.

In Vivo Efficacy of Gel Formulations to Protect Against Infection Caused by Herpes Viruses (Intravaginal Model)

The efficacy of gel formulations to prevent the genital transmission of HSV-2 has been evaluated in a murine intravaginal infection model. In brief, female Balb/c mice aged 4 weeks were used for this study. To increase susceptibility of mice to herpes, 2.5 mg of progesterone (Depo-Provera) was administered subcutaneously to each mouse 7 days prior to and one day prior to inoculation with HSV-2. Anesthetized mice were inoculated with 5 μl of $2.4 \times 10^7$ pfu/ml of HSV-2 (strain 333) after swabbing the vagina with a calcium alginate thin tipped swab. To determine the efficacy of the gel formulations to block herpes infection, 15 μl of the gel was delivered with a pipette tip into the vagina a few minutes prior to the inoculation. The pipette tip was moved in and out four times to simulate stirring action of sexual intercourse while being cautious not to cause any bleeding.

Figure 9A:
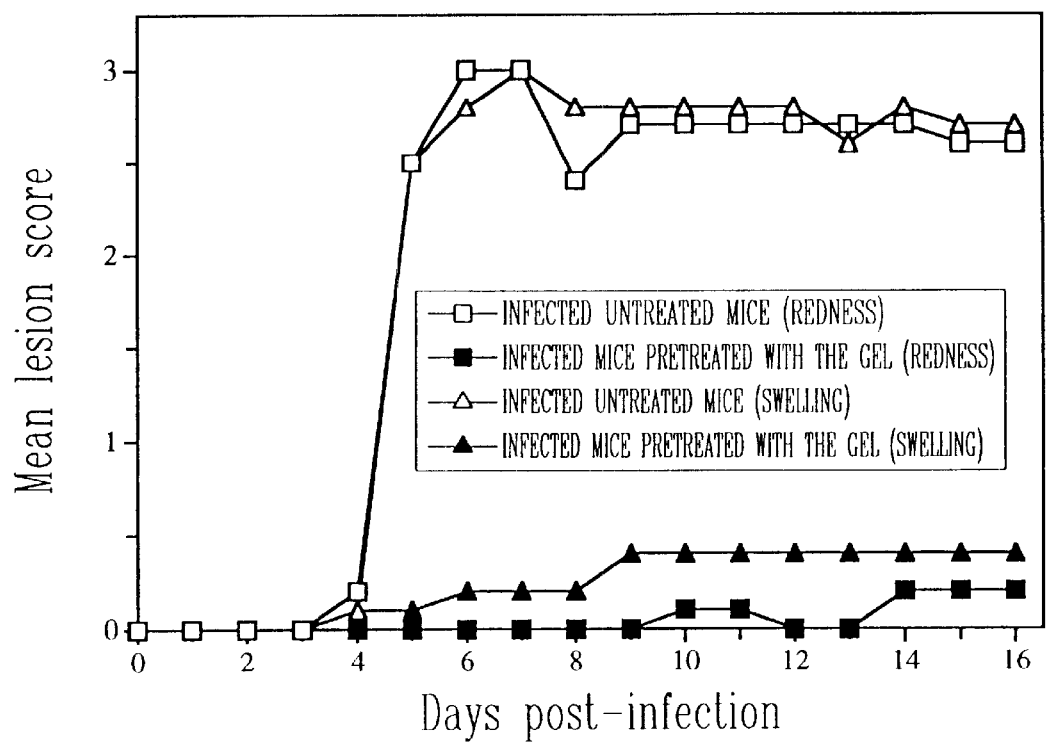
FIG. 9 shows the time evolution of mean lesion score (Panel A) and survival (Panel B) of mice infected intravaginally with HSV-2 (strain 333) pretreated with the gel alone (■, ▼, ●) 5 min prior to infection. Infected untreated mice were used as control (□, △, ○). Results are mean of 8 animals per group.
Figure 9B:
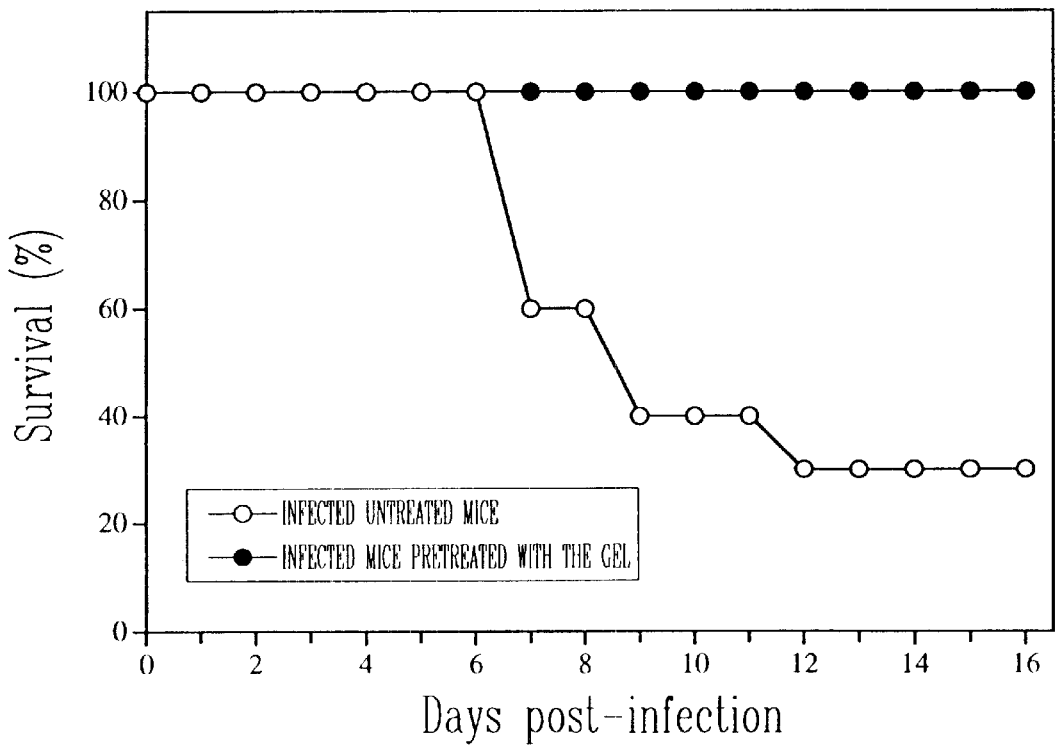

FIG. 9 shows the mean lesion score and survival rate of infected untreated mice and of mice pretreated intravaginally with the gel alone prior to infection with HSV-2 (strain 333). Four days post-infection, infected untreated animals demonstrated perineal oedema and redness and by 6 to 12 days, most of them died of encephalitis. Of prime importance, all mice pretreated with the gel alone survived the infection and did not demonstrate any sign of illness up to 16 days post-infection. The presence of the gel alone could thus abolish HSV-2 infection.

Figure 10:
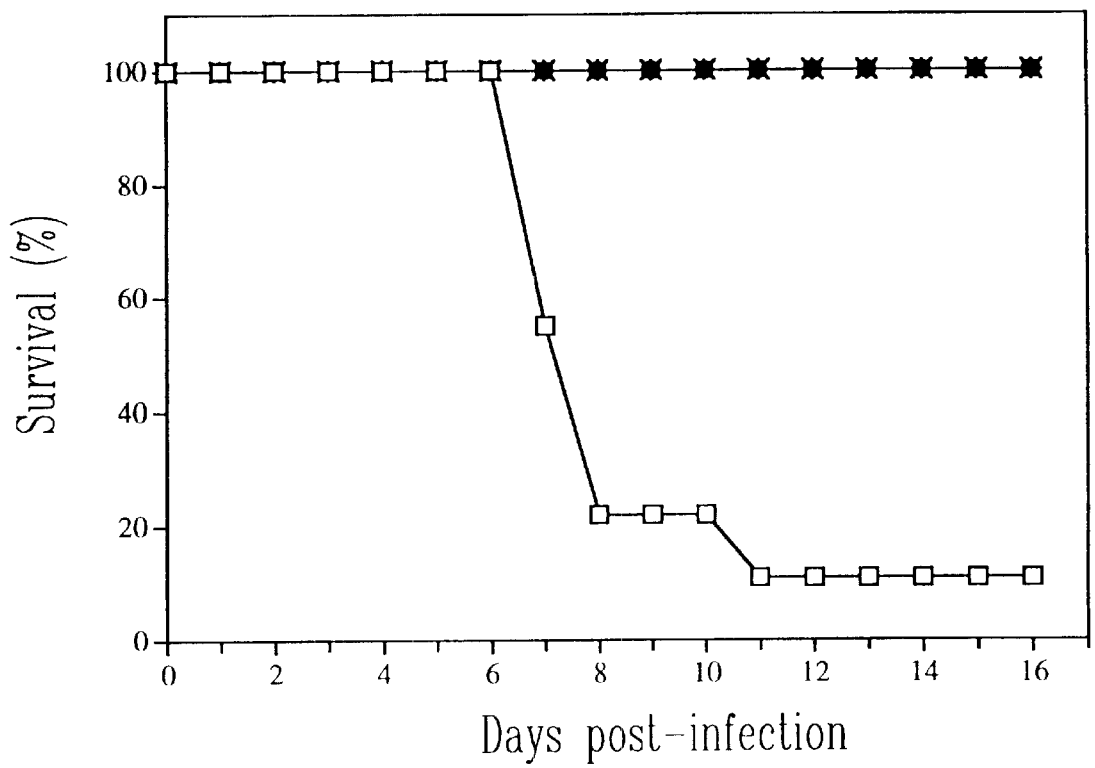
FIG. 10 shows: the time evolution of survival of mice infected intravaginally with HSV-2 (strain 333) pretreated with 2.5% SLS (*) or gel+2.5% SLS (●) 5 min prior to infection. Infected untreated mice were used as control (□). Results are expressed as mean of 8 animals per group.

FIG. 10 shows the survival rate of infected untreated mice and of mice pretreated intravaginally with 2.5% SLS or gel containing 2.5% SLS prior to infection with HSV-2 (strain 333). Four days post-infection, infected untreated animals demonstrated perineal oedema and redness and by 6 to 12 days, most of them died of encephalitis. Of prime importance, all mice pretreated with either 2.5% SLS alone or gel containing 2.5% SLS survived the infection and did not demonstrate any sign of illness up to 16 days post-infection. Taken together, these results clearly indicate that the use of our gel preparation could represent an innovative preventive measure to reduce the sexual transmission of herpes, HIV and other pathogens causing STDs.

FIG. 11 shows the survival rate of infected untreated mice and of mice pretreated intravaginally with gel containing various compounds prior to infection with HSV-2 (strain 333). Those compounds were selected to represent other sulfated and non-sulfated compounds having or not detergent properties. They also represent various ionic (anionic and cationic) and non-ionic compounds. This screening approach was aimed to find other potential candidate microbicides. Results showed that the gel formulation containing 2.5% lauroyl sarcosine gave complete protection against infection (100% survival). On the other hand, the gel formulations containing 2.5% benzalkonium chloride, 5% polyoxyethylene 40 stearate and 5% guanidine gave 60, 60 and 30% survival, respectively. Our preliminary results showed that lauroyl sarcosine has good potential as a candidate microbicide that we are actually exploring now. However, other compounds such as benzalkonium chloride, polyoxyethylene 40 stearate and guanidine that showed partial microbicidal potential can also be explored by optimizing their concentration for better efficacy. Alternatively, combinations of these compounds may also provide optimal efficacy, if compatible. Without being bound to any theory, it is envisageable that the combination of a detergent with a chaotropic agent may provide for an efficacy as good as or even better than SLS. These are specific examples of potential microbicides, but are in no way intended to limit the scope thereof.

Design of Applicator for Vaginal/ano-rectal Delivery of Formulations

As mentioned above, it is an object of the present invention to provide formulations to prevent infection and/or abnormal conditions of mucosae and/or skin caused by any pathogen and/or any disease. For vaginal applications, any topical formulations should be administered using an applicator which allows uniform distribution of the content to the entire vagina (delivery to sides) and cervix (delivery to front) for maximal efficacy. Therefore, we have designed a unique applicator which allows about 360° distribution of its content into the vagina and far to the cervix which is a great improvement over existing conventional vaginal applicators which deliver contents only to front (cervix area). The different objectives to achieve and the main characteristics that our unique applicator should have to deliver topical formulations include:

a) Uniform distribution of topical formulations as liquid or gel to the entire vagina/cervix
b) Efficient and rapid delivery of its content
c) Resistance to temperature variations (−40 to 60° C.)
d) Compatibility of the polymer of the applicator with the gel formulations
e) Ease of sterilization
f) No leakage
g) Ease of manipulation and insertion
h) Resistance to breakage, to expansion of content and to vibrations due to transport
i) Compatibility with agents and/or conditions present in the surrounding environment Technical Background and Strategy The efficacy of a formulation to block the sexual transmission of pathogens causing STDs depends i) on the nature of the formulation to be delivered and ii) on its ability to cover the entire vaginal/cervix area. Unlike other products, we have a unique formulation with thermoreversible property which is delivered in liquid form assuring a good penetration of the formulation into the smallest irregularities of the vaginal/cervical mucosae. For maximum protection, such a formulation should cover the entire vagina/cervix. However, the existing conventional vaginal applicators have a unique hole at the tip so that the content is delivered only to the cervix area excluding the vagina, limiting therefore its efficacy. Our unique vaginal applicator will have multiple holes and/or slots (at the tip and on the sides) to deliver our formulation or any other film-forming component, gel, cream, ointment and/or antimicrobial, bactericidal, virucidal, chemotherapeutic, antiinflammatory, antineoplastic, or immunomodulatory agent, detergents, microbial adsorption inhibitor, skin penetration enhancing agent, cytokine, antigen, vaccines, or combination of them thereof to treat or prevent STDs, cancer or any other disease, to uniformly cover both the vagina and cervix for maximal protection. Literature searches revealed that there is no applicators or similar products on the market having such a design which allow delivery of their content to the entire vagina/cervix.

Characteristics of our Applicator

All of the existing vaginal applicators deliver formulations in a form of gel/cream which has the disadvantage of not covering the whole vagina/cervix area. On the other hand, our formulation has an important thermoreversible property being liquid at room temperature and gelifying at body temperature. When delivered as liquid, our formulation would cover the whole vagina/cervix and it would penetrate through the smallest irregularities of vaginal and cervical mucosae. For our unique formulation or any other film-forming component, gel, cream, ointment and/or antimicrobial, bactericidal, virucidal, chemotherapeutic, antiinflammatory, antineoplastic, or immunomodulatory agent, detergents, microbial adsorption inhibitor, skin penetration enhancing agent, cytokine, antigen, vaccines, or combination of them thereof to treat or prevent STDs, cancer or any other disease, we need a unique applicator to deliver from the very end as well as sides to cover the whole vagina/cervix which is the key factor for offering maximal protection against pathogens causing STDs. The major characteristics of the applicator are discussed below (see also Table 3):

a) Uniform Distribution of Topical Formulations as Liquid or Gel to the Entire Vagina/cervix The applicator must deliver the formulation uniformly and must cover the whole vagina/cervix area by delivering through apical and lateral holes. Furthermore, the applicator should deliver sufficient amount to cover both cervix and vagina. This will allow maximal protection of individuals against pathogens causing STDs.

b) Efficient and Rapid Delivery of its Content

Most existing vaginal applicators deliver only a fraction of its content limiting the efficacy of the formulation. Therefore, the applicator must deliver either all of its content without leaving residual material in the reservoir or deliver the quantity required for sufficient coverage of all target mucosae. This will be achieved through the design of the reservoir and calculating the average force of the fingers pressing on it to release its content. The time of delivery will vary depending on whether the content is delivered as a liquid, semi-viscous or gel. However, the delivery of applicator's content must be rapid.

c) Resistance to Temperature Variations (−40 to 60° C.)

The applicator must resist temperature variations because storage and transport environments will vary greatly from one country to another. It should be designed so that the applicator and the formulation remain unchanged under temperature conditions ranging from −40 to 60° C.

d) Compatibility of the Polymer of the Applicator with the Gel

The polymer used for the development of the vaginal applicator should not affect the properties of the gel formulation (stability, viscosity parameters, non-cytotoxicity, efficacy to block pathogens, etc.).

e) Ease of Serilization

The applicator design and material must ensure that it can be sterilized using a suitable method and should not result in changes in the characteristics of it or its content.

f) No Leakage

The applicator must be leak-proof under storage and transport conditions. If boxes are stacked on top of each other, the applicator should not leak its content.

g) Ease of Manipulation and Insertion

The applicator must be user friendly, easy to manipulate and easy to insert without causing any discomfort to its user. Furthermore, it should be appealing to users.

h) Resistance to Breakage, to Expansion of Content and Vibrations Due to Transport The applicator should resist breakage if it falls from the user's hand or when it is handled during transport. It should also resist expansion of its content. Furthermore, the applicator should be stable and resist to vibrations during transport.

i) Compatibility with Agents and/or Conditions Present in the Surrounding Environment The applicator should resist to the agents and/or various conditions present in the surrounding environment. For example, it should not be affected by vaginal acidic pH, vaginal discharges or other similar conditions.

TABLE 3

Desired functions and target values of the applicator

| No | Function | Description | Target value |
|---|---|---|---|
| 1 | Distributes formulation as liquid, semi-viscous, gel, cream, ointment or any film-forming component | Once introduced, proceed to expulsion and distribution of formulation | Quantity about 3–5 ml |
| 2 | Distributes formulation uniformly | Distributes formulation to cover the whole vagina/cervix | Distributes over about 3600 in vagina and over about 3600 in cervix |
| 3 | Contains formulation as liquid, semi-viscous, gel, cream, ointment or any film-forming component | Applicator has reservoir | Minimal content of injected volume |
| 4 | Leak-proof | No leakage from package and after initial manipulation | 0 ml |
| 5 | Easy to manipulate | Applicator can be held easily and is user friendly | Favourable opinion of volunteers (7/10) |
| 6 | Easy to insert | Applicator inserted without pain and minimal resistance | Average diameter of about 0.5 inch (12.5 mm) |
| 7 | Delivers to vagina/cervix | The applicator length allows it to reach cervix | Average length of about 4.5 inch (115 mm) including reservoir and holding |
| 8 | Resists to fall | The applicator should not break and content should not leak if it falls from user's hands | Fall of about 60 inch (1.5 m) |
| 9 | Resists to surrounding environmental conditions | The applicator should not be affected by its content, vaginal secretions or packaging material | Data from manufacture of thermoplastic resin |
| 10 | Not toxic and does not affect surrounding environmental conditions | Does not affect the composition or quality of formulation; it should also not affect the surrounding environment | Data from manufacture of thermoplastic resin and topical formulation owner |
| 11 | Resists to vibration during transport | The applicator and reservoir should not be damaged and should operate normally after transport | Standards to be verified |
| 12 | Be efficient | Be operational (delivers content and distributes evenly without failure) | Favourable opinion of volunteers (9/10) |
| 13 | Delivers fast | Content is rapidly ejected from applicator | About 5 sec |
| 14 | Resists to temperature variation | The applicator should not be affected by temperature variations | −40° C. to +60° C. |
| 15 | Can be rinsed under water | Can be rinsed if drops from user's hands | Data from manufacture of thermoplastic resin |
| 16 | Sterilizable | Suitable method to be selected | Standards to be verified |

The following are examples of some different concepts which are intended to describe some of the general design possibilities of the applicator, but are in no way intended to limit the scope thereof. It is important to mention that the final shape of the applicator can differ from the examples given herein. It is deemed that such designs can be modified to suit anorectal application.

FIGS. 12–15 illustrate specific examples of applicators according to an aspect of the present invention. The following disclosure describes four embodiments of applicators illustrated in these figures.

Generally stated, the present applicator is designed to uniformly deliver any formulation as liquid, semi-viscous, gel, cream, ointment or any other film-forming component described herein above into a mucosal cavity, with the smallest residual amount thereof left within the applicator. The present applicator comprises a longitudinally extending body which has proximal and distal ends. The proximal end is located close to the external site of the mucosal cavity accessible to the patient. The body has external perforations, made as a series of slots or holes, for uniform distribution of any formulation as described above to be delivered to the patient's mucosal cavity. Upon insertion of the applicator and expulsion of the formulation in the mucosal cavity, the formulation which is contained in a reservoir, should advantageously travel through a diffusion channel having a small volume, prior to being expelled through the perforations. Indeed, this allows both the rapid expulsion of the formulation and the minimization of the quantity of formulation left in the applicator after expulsion.

The diffusion channel is created by a free space between two walls defining the body. The first wall is an external wall of the body and includes apertures. The second, non perforated, internal wall is provided inside the first wall to create the diffusion channel. The internal wall is so configured and sized that it can be slidably inserted into the first wall. Alternatively, the internal wall, sized to be smaller than the first one, may be integrally molded with the external wall of the body.

The internal wall has a proximal end which is an inlet end for the formulation into the diffusion channel. A directing element may also be provided to direct the formulation into the inlet end of the diffusion channel. The directing element therefore prevents entry of the formulation into another compartment than the diffusion channel.

A reservoir capable of receiving the formulation is also part of the applicator. The reservoir can be located near the body of the applicator or inside the body. The reservoir is operatively connected to an expulsion element. The expulsion element is itself connected to the proximal end of the body through a connector element. The expulsion element is actuated by the patient. Upon application of compression, pull or push movements, the expulsion element releases the content of the reservoir, which is contacted with the proximal entry end of the diffusion channel. The formulation therefore travels into the diffusion channel to the mucosal cavity, being expulsed through the perforations.

Turning now to FIGS. 12*a*–12*d* of the appended drawings, a first embodiment of an applicator according to an aspect of the present invention will be described. FIG. 12*b* shows an exploded view of this first applicator. The external wall (1) of the body of the applicator shows perforations (2) (only one shown) made as one single slot extending from one side of the body through the opposite side with no interruption at the distal end of the external wall (1). The longitudinal slot therefore defines lateral and distal perforations. In this embodiment, the reservoir and the expulsion element are one single element (3) made of a compressible material. The formulation is contained in the reservoir which ejects its content by pressing it with fingers. The reservoir is terminated by a membrane of low resistance to compression (4). The reservoir being the expulsion element, it is connected to the proximal end of the body through a connector element (5) represented by a screwable or snap-in connector element. In this particular embodiment, the internal wall (6) of the body is provided as a separated element dimensioned to be smaller than the external wall. The proximal end of the internal wall terminates with a protruding collar that sits onto the connector element formed at the proximal end of the external wall. The proximal part of the internal wall comprises a closing element (7) which closes the internal lumen formed by the internal wall. The closing element may have the shape of a disc. Alternatively, the proximal end of the internal wall may be integrally molded with the latter to be simply closed. Concentric to this closing element, there is an open concentric element (8) located at the periphery of the closing element. These elements provide for a generally called directing element, which directs the formulation into the diffusion channel formed between the internal and the external walls and away from the internal surface of the internal wall (6). FIG. 12*c* also shows a tapered element (9), located at the centre of the directing means, provided to break the membrane (4) when adequate pressure is applied.

A second embodiment of the applicator is illustrated in FIG. 13. The same peripheral and internal walls as in FIG. 12 are used in this applicator. However, a plurality of slots regularly spaced from each other are provided in the external wall. In this specific version, the expulsion element and the reservoir are also one single element. However, the expulsion element is not a compressible reservoir. It is rather a piston-like structure (10) which comprises the formulation provided in a pouch (11). In this embodiment, the connector element (5) is telescopically insertable in the piston-like structure (10). The pouch is made of a material of low resistance to compression. To break this membrane, a tapered element is provided at the proximal end of the internal wall. FIG. 13 shows this tapered element (9) as a disc provided with a pointed portion. The disc sits on the proximal end of the internal wall, the pointed portion facing the pouch (11). In use, the piston-like structure (10) is pressed by the user, the membrane is thus pierced by the pointed portion, and the formulation is thus forced through the diffusion channel, and expelled through the perforations.

FIG. 14 illustrates a third embodiment of the present applicator. While the two previous embodiments show a reservoir located near the proximal end of the diffusion channel, this third embodiment shows a reservoir (12) provided away from the proximal end of the diffusion channel. In this: case, a seat (13) located away from the reservoir is provided. The seat is operatively connected to the piston (14) located proximally to the reservoir (12). The user pulls the piston and therefore compresses the reservoir, the content of which is engaged into the proximal inlet end of the diffusion channel. The formulation is expulsed through perforations made in the external wall of the body of the applicator, shown in FIG. 14 as a plurality of holes (2). The holes are spaced in such a way that the formulation is uniformly distributed into the mucosal cavity. The holes are located in the longitudinal section of the external wall as well as to the distal end thereof. FIG. 14 further shows that the internal and external walls of the body of the applicator may be integrally formed. Alternatively, the internal wall may also take the shape of the one shown in FIGS. 12 and 13, without the need of a tapered element. The reservoir may include a membrane of low resistance to compression in such a way that, when compressed by the pull movement of the piston (14), the membrane breaks and discharges its content into the diffusion channel. In this embodiment of the applicator, the directing element is formed by the proximal entry end of the diffusion channel and a closing element located this time at the proximal end of the body (not shown).

FIG. 15 shows a fourth embodiment of the applicator according to an aspect of the present invention. In this embodiment, the reservoir and expulsion element are a single element. A membrane (4) of low resistance is located close to the proximal end of the body (1). The external wall of the applicator comprises slots that are practised as a plurality of grooves. The internal wall (6) is integrally formed with the outer wall. The internal wall terminates at its proximal end with a tapered element (15). The reservoir/piston (16) has a diameter which is slightly larger than the external diameter of the internal wall, but smaller than the internal diameter of the external wall of the body of the applicator. In use, the reservoir is slidably engaged between the two walls, the membrane is pierced and its contents are forced in to the diffusion channel and in the perforations located on the sides and at the distal end of the external wall.

It is to be noted that in all the above described embodiments, the directing element may be integrally formed with the proximal end of the internal wall of the body or be provided as a closing element or disc to block the passage of the formulation into the internal lumen formed by the internal wall and to direct the flow of the formulation into the diffusion channel.

Further, for ease of use, grasping elements may be provided in some embodiments to help the user maintain the applicator in place while actuating the expulsion element. More specifically, in the second embodiment, the grasping element is defined by the annular collar (17) formed at the outer periphery of the connector element (5). The annular collar has an external thickness such that the user has enough space to grasp the distal end of the collar between fingers and push the piston with another finger. In the third embodiment, the grasping element is provided at the proximal end of the piston (see numeral 18). The external wall of the body being of a larger section than the piston, the user can hold the body of the applicator by its proximal end with one hand and pull the piston with another. Finally, in the fourth embodiment, the grasping element is provided as an elliptic handle (19) located at the proximal end of the body of the applicator and surrounding the connector element. This handle may be held between two fingers, while the piston is pushed with another finger.

Examples Involving our Poloxamer Formulations for Treatment of Infection

For the purpose of testing the efficacy of our gel formulations in a murine model of cutaneous HSV-1 infection, the solutions were prepared within a phosphate buffer (0.2 M, pH 6) to be compatible with the pH of the skin.

Comparative Efficacy of Topical Formulations of Foscarnet, Acyclovir, and of Zovirax Ointment Against HSV-1 Cutaneous Lesions in Mice The efficacy of our different topical formulations has been evaluated in a murine model of cutaneous HSV-1 infection. In brief, female hairless mice (SKH1; Charles River Breeding Laboratories Inc., St-Constant, QC, Canada), 5–7 weeks old were anesthetized by intraperitoneal injection of a mixture containing 70 mg/kg ketamine hydrochloride and 11.5 mg/kg xylazine. The virus was inoculated on the lateral side of the body in the left lumbar skin area. The skin was scratched six times with a 27 gauge needle held vertically in a crossed-hatched pattern. Fifty $\mu$l of viral suspension (HSV-1 strain F, $1.5 \times 10^6$ plaque forming units (PFU)/ml) was rubbed for 10 to 15 sec on the scarified skin area with a cotton tipped applicator saturated with culture medium [minimum essential medium (MEM) supplemented with 100 U/ml of penicillin-streptomycin, 2 mM L-glutamine and 2% fetal bovine serum (MEM-E+2% FBS)]. The scarified area was protected with a corn cushion which was maintained on the mice body with surgical tape. The porous inner wall of the aperture of the corn cushion was impermeabilized with tissue adhesive prior to use to prevent absorption of the drug. The aperture of the corn cushion was also closed with surgical tape. Mice were then returned to their cages and observed twice daily.

Different treatment regimens were evaluated in this study. Briefly, the tape closing the aperture of the corn cushion was removed and the scarified area was cleaned with a cotton tipped applicator saturated with cold water. Fifteen $\mu$l of the different formulations was applied onto the scarified area. The aperture of the corn cushion was closed with surgical tape to avoid rapid removal of the drug by the mice. This procedure also prevents accidental systemic treatment that could occur due to potential licking of the treated lesions. The efficacy of the different formulations was evaluated using lesion scores and survival.

Figure 16A:
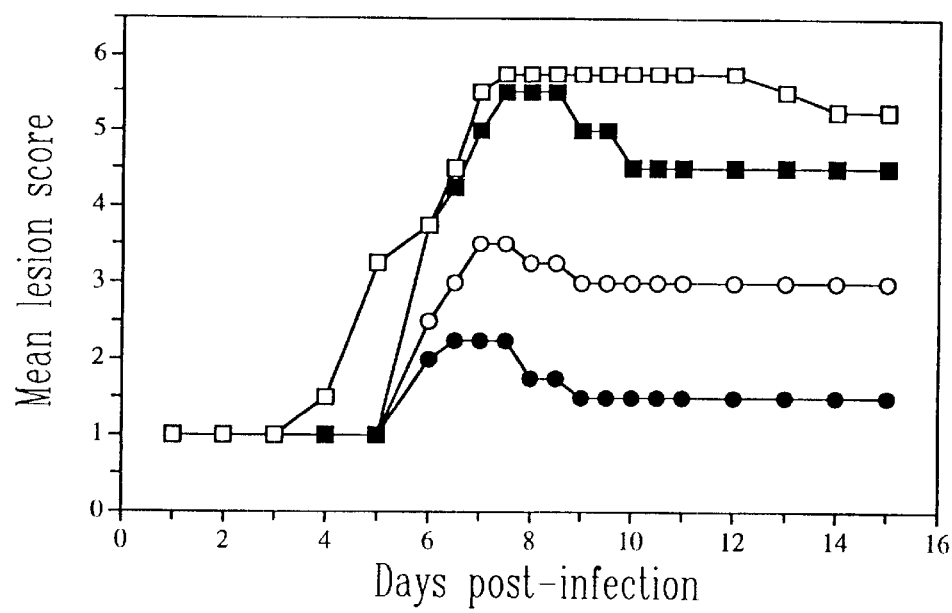
FIG. 16 shows the time evolution of mean lesion score (Panel A) and survival (Panel B) of hairless mice infected cutaneously with HSV-1 and treated topically with the poloxamer alone (■), 0.5% foscarnet in aqueous solution (○) or poloxamer containing 0.5% foscarnet (●). Infected untreated mice were used as control (□). Treatment started 24 h after infection and was repeated 3 times daily for 4 days. Values are expressed as mean of 4 animals per group.
Figure 16B:
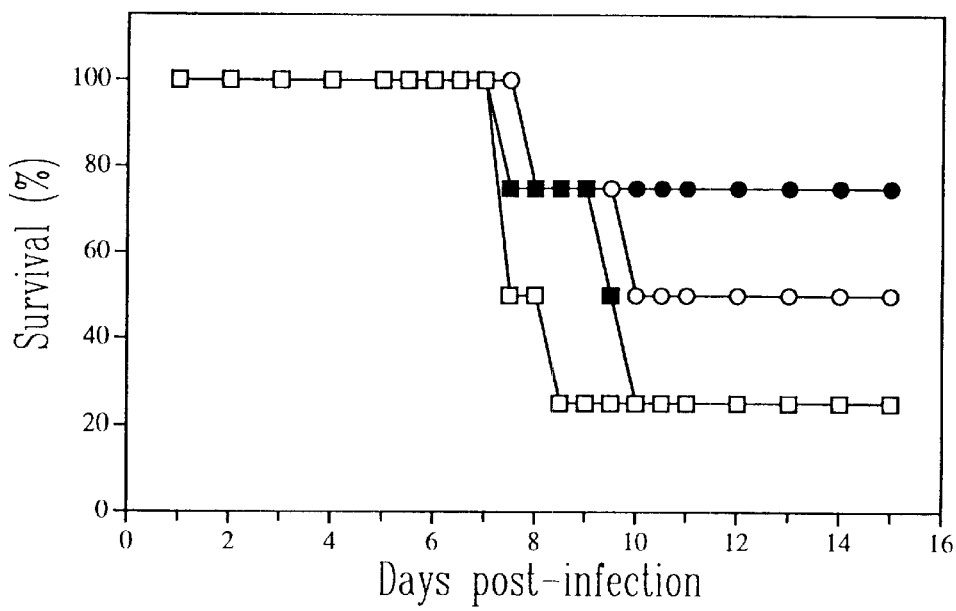

FIG. 16 (Panel A) shows the time evolution of mean lesion score of infected untreated mice or mice treated with foscarnet in solution or incorporated into poloxamer. Treatment was started 24 h after infection and was repeated 3 times daily for 4 days. In mice treated with the poloxamer alone, we observed a pattern largely similar to that seen with untreated mice except that the regression of cutaneous lesions seemed to go faster in the latter group. In mice treated with a solution of 0.5% foscarnet, we observed a large reduction of mean lesion score which was more pronounced when the drug was associated to the poloxamer formulation. FIG. 16 (Panel B) shows the corresponding survival for infected untreated mice and mice treated with the drug formulations. Death by encephalitis occured in 75% of untreated infected mice between day 7 and day 8. The mortality was similar in mice receiving the poloxamer alone and occured between day 8 and 10. Half of the mice treated with foscarnet in solution survived the infection. Of prime interest, 75% of mice treated with the poloxamer formulation of foscarnet survived the infection (p<0.05).

Figure 17A:
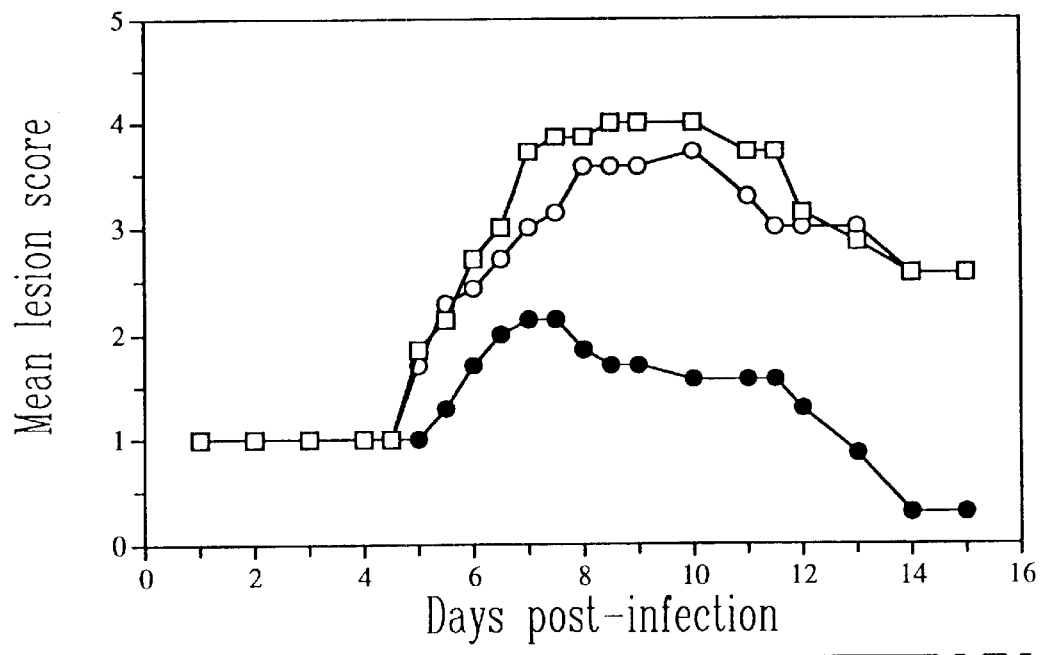
FIG. 17 shows the time evolution of the mean lesion score (Panel A) and survival (Panel B) of hairless mice infected cutaneously with HSV-1 (strain F) and treated 24 h postinfection with a single application of either poloxamer containing 5% acyclovir (●) or Zovirax® ointment (○). Infected untreated mice (□) were used as controls. Values are expressed as mean of 7 to 10 animals per group.
Figure 17B:
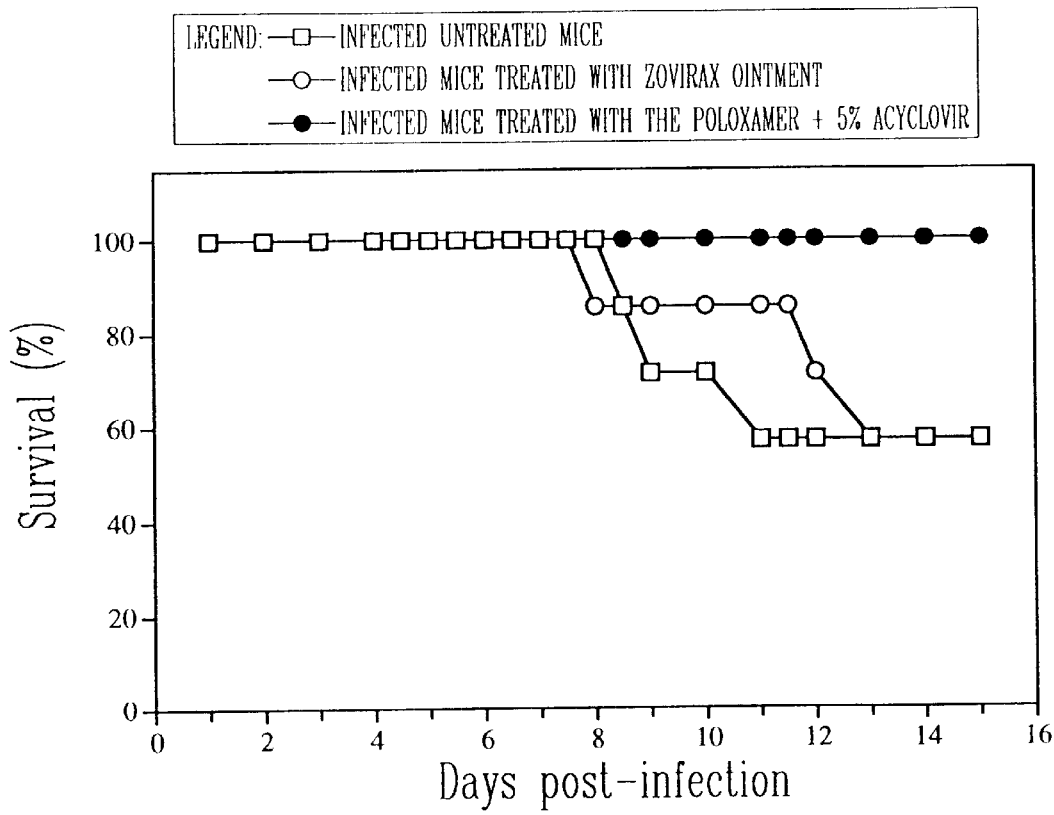

FIG. 17 (Panel A) shows the time evolution of the mean lesion score of infected untreated mice and of mice treated with a single application at 24 h post-infection of the poloxamer containing 5% acyclovir or the Zovirax® ointment. Of prime interest, the poloxamer formulation containing 5% acyclovir demonstrated a good efficacy against the development of cutaneous lesions in mice, whereas the Zovirax® ointment exerted only a modest effect. However, acyclovir incorporated into the poloxamer significantly reduced the lethality (p<0.05), but not the Zovirax® ointment (Panel B). The higher efficacy of the poloxamer formulation of acyclovir over the commercial Zovirax® ointment highly suggests that the poloxamer could be a better vehicle for the topical delivery of this drug.

Figure 18A:
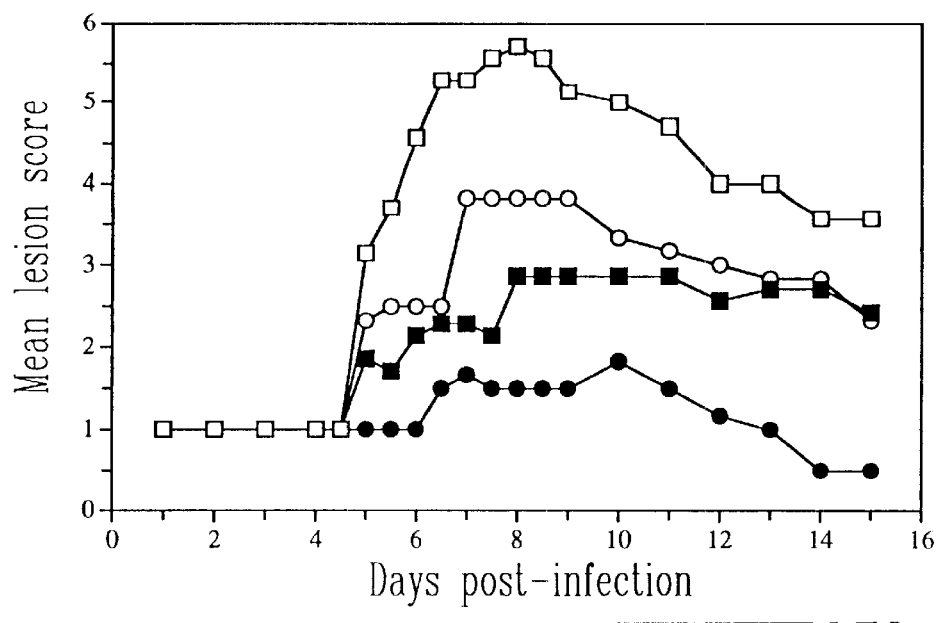
FIG. 18 shows the time evolution of the mean lesion score (Panel A) and survival (Panel B) of hairless mice infected cutaneously with HSV-1 (strain F) and treated with the poloxarner alone (■), poloxamer containing 5% acyclovir (●), or with Zovirax® ointment (○). Infected untreated mice (□) were used as controls. Treatment started 5 days after the infection and was repeated 3 times daily for 4 days. Values are expressed as mean of 7 to 10 animals per group.
Figure 18B:
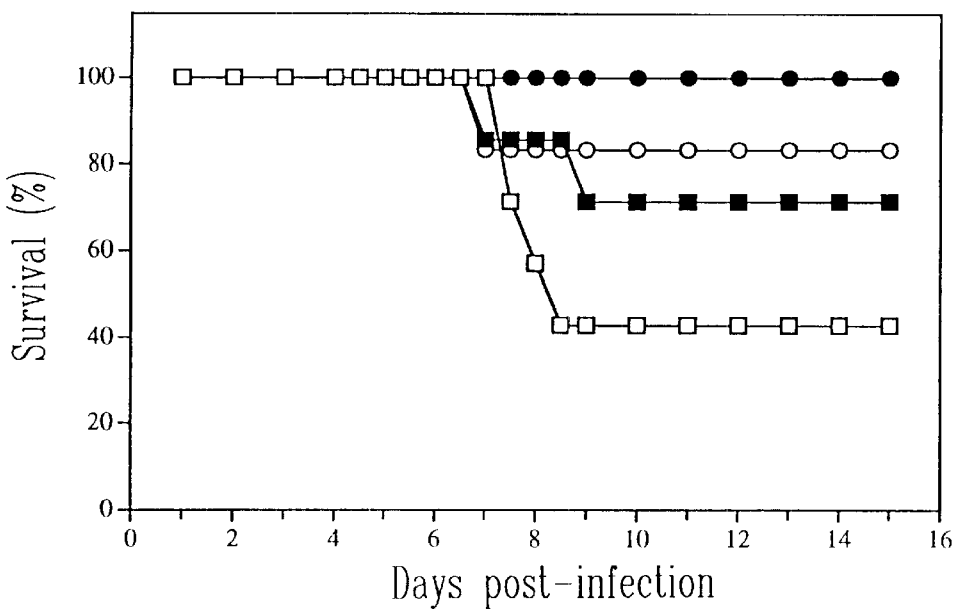
Figure 19D:
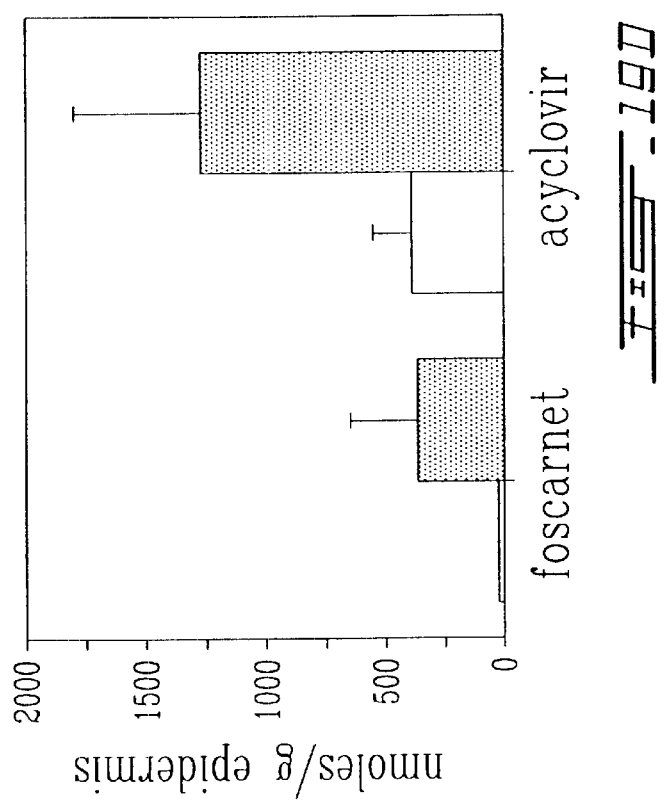
FIG. 19 shows the distribution of foscarnet (△, ▼) and acyclovir (○, ●) in skin tissues of uninfected (Panels A, C, E) and infected (Panels B, D, F) mice at 24 h after their topical application, either in phosphate buffer (open symbols) or within the poloxamer (filled symbols). Panels A and B show the distribution of foscarnet and acyclovir in the stratum corneum strips. Panels C and D show the concentration of foscarnet and acyclovir in the epidermis whereas panels E and F show the concentration of foscarnet and acyclovir in the dermis. Values are expressed as mean of 4 to 6 animals per group.
Figure 19C:
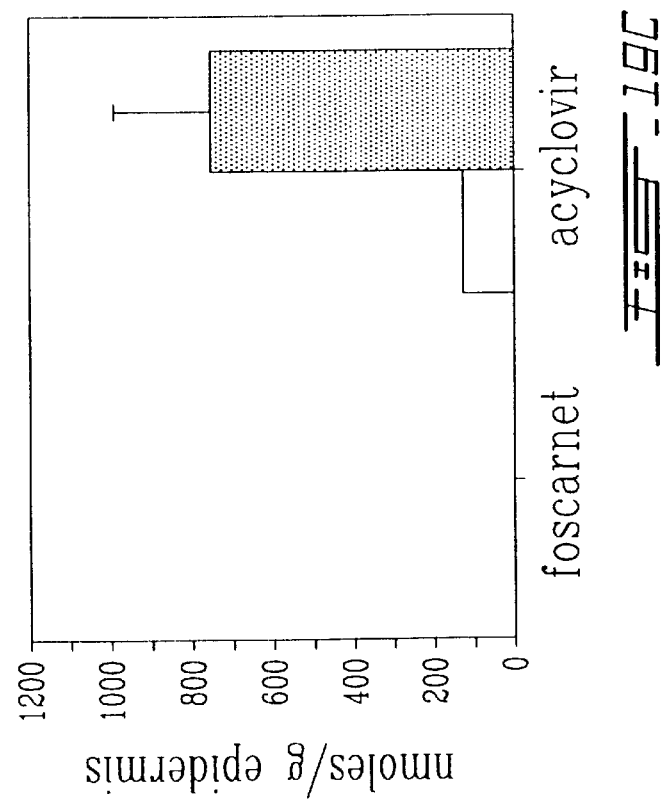
Figure 19F:
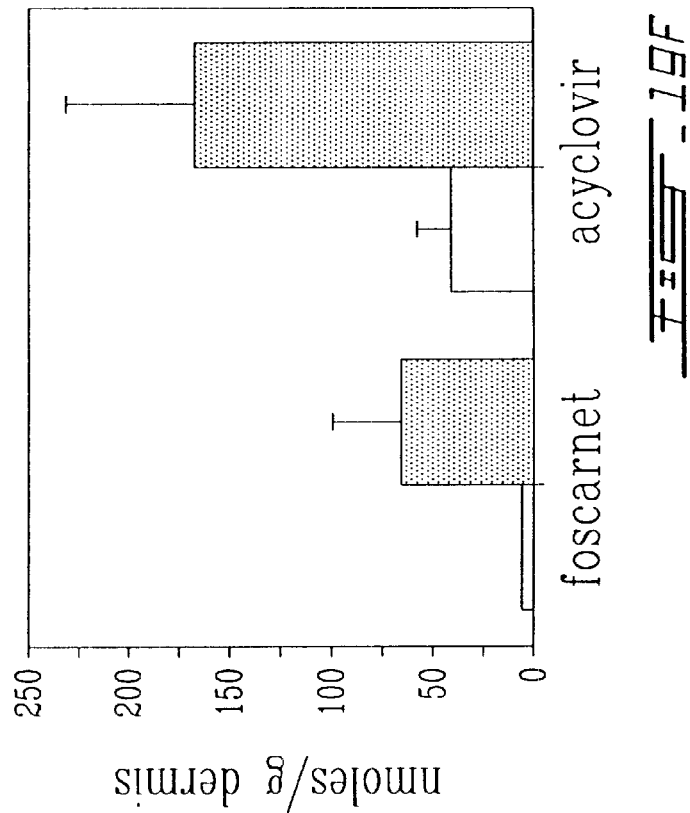
Figure 19E:
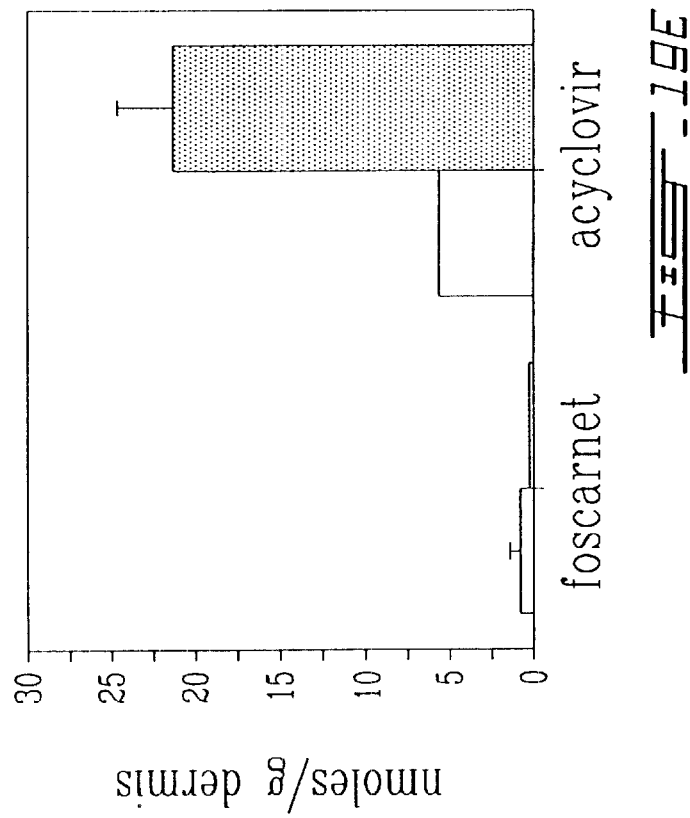

FIG. 18 (Panel A) shows the time evolution of the mean lesion score of control mice and of mice treated 3 times daily during 4 days and initiated 5 days post-infection with the poloxamer alone, poloxamer containing 5% acyclovir or the Zovirax® ointment. In mice receiving the poloxamer alone, a reduction in the mean lesion score compared to infected untreated mice was observed. Treatment with the Zovirax® ointment exerted only a modest effect. However, a marked reduction of the mean lesion score was observed for mice treated with the poloxamer formulation containing 5% acyclovir when compared to untreated infected animals. Of prime interest, all mice treated with the poloxamer containing 5% acyclovir survived the infection (p<0.001) (FIG. 18, Panel B). Treatment with Zovirax® ointment increase to a lesser extent the survival of infected mice (p<0.05).

In Vivo Skin Penetration of Antivirals

FIG. 19 shows the distribution of foscarnet and acyclovir in skin tissues of uninfected (Panels A, C, E) and infected (Panels B, D, F) mice at 24 h after their topical application, either in phosphate buffer or in the poloxamer matrix. The distribution of both formulations of foscarnet and of the buffered solution of acyclovir was similar in the stratum corneum tape strips of uninfected and infected mice. In contrast, the incorporation of acyclovir into the poloxamer markedly increased the amount of drug recovered in the stratum corneum of both uninfected and infected mice; the increased drug penetration being more pronounced in infected mice. No or negligible amounts of foscarnet were found in the underlying epidermis and dermis of uninfected mice irrespective of the carrier used for the drug application. The concentration of foscarnet in the epidermis and dermis of infected mice was significantly higher when the drug was incorporated within the poloxamer. The concentration of acyclovir was higher than that of foscarnet in the epidermis and dermis of both uninfected and infected mice irrespective of theicarrier used. The concentration of acyclovir incorporated within the poloxamer in the epidermis of uninfected mice was 6.1-fold greater than that of the drug in the buffered solution. Infection of mice did not significantly increase the amount of acyclovir in the epidermis. The concentration of acyclovir in the dermis of infected mice was 7.9-fold greater than that in uninfected mice when the drug was administered in the poloxamer matrix.

Figure 20:
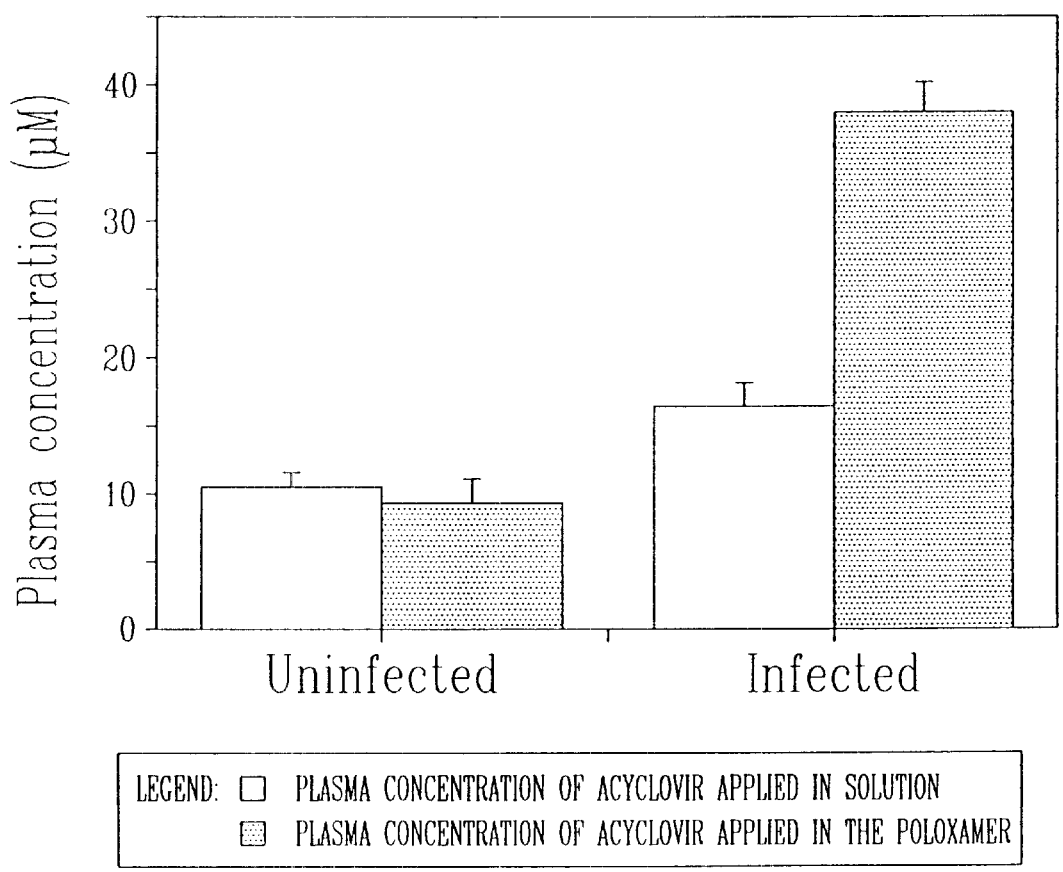
FIG. 20 shows the concentration of acyclovir in plasma of uninfected and infected mice at 24 h after its topical application, either in phosphate buffer (open bars) or in the poloxamer (filled bars). Values are expressed as mean of 4 to 6 animals per group.

FIG. 20 shows the concentration of acyclovir in plasma of uninfected and infected mice at 24 h after its topical application, either in phosphate buffer or in the poloxamer matrix. Similar concentrations of acyclovir were found in plasma of uninfected mice for both formulations. Infection of mice markedly increased the concentration of acyclovir in plasma, especially when the drug was incorporated within the poloxamer matrix for which a 4-fold increased concentration was reached. The concentration of acyclovir in the plasma of infected mice was 2.1 fold greater when the drug was incorporated into the poloxamer matrix.

Figure 21A:
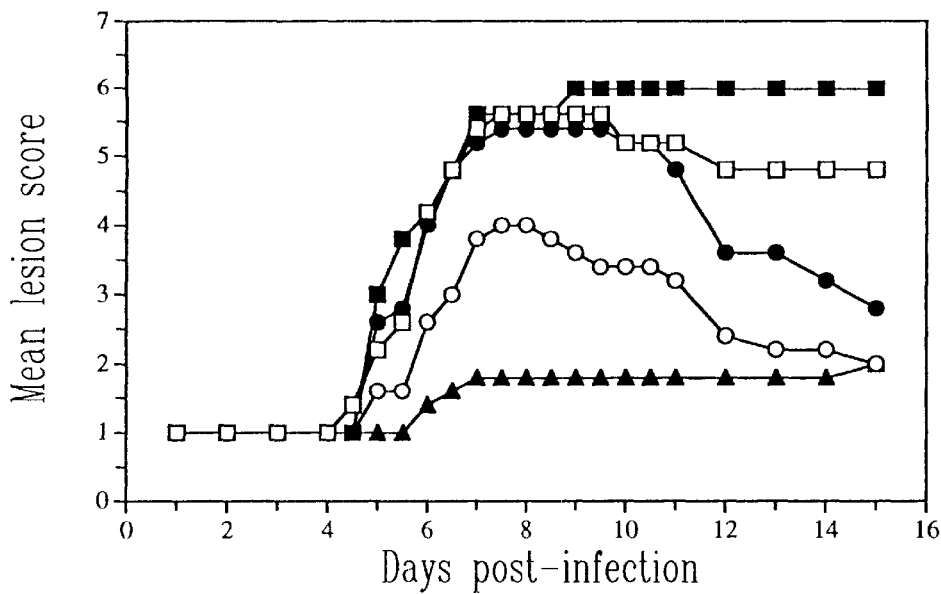
FIG. 21 shows the time evolution of mean lesion score (Panel A) and survival (Panel B) of hairless mice infected cutaneously with HSV-1 (strain F) treated with the poloxamer alone (■), poloxamer containing 3% foscarnet (○), poloxamer containing 5% SLS (●) or poloxamer containing 3% foscarnet+5% SLS (Δ). Infected untreated mice (□) were used as controls. Results are expressed as mean of 5 animals per group.
Figure 21B:
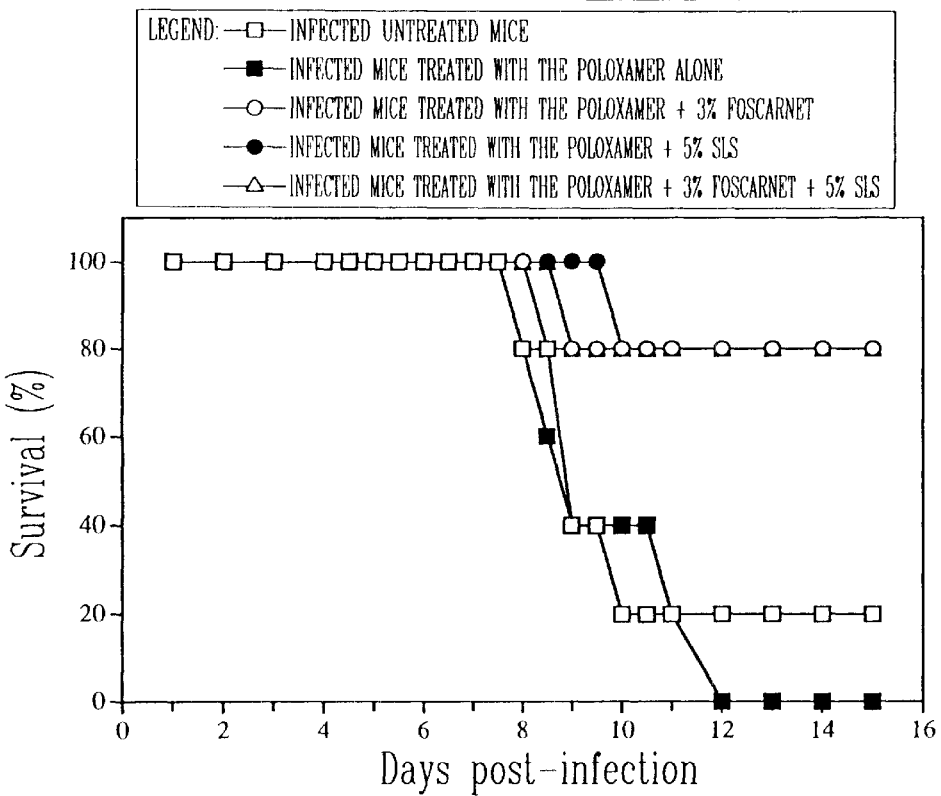

Effect of SLS on the Efficacy of Poloxamer Formulations Containing Foscarnet or Acyclovir Against HSV-1 Cutaneous Lesions in Mice The influence of SLS on the efficacy of poloxamer formulations containing foscarnet against HSV-1 infection has also been evaluated in mice. FIG. 21 (Panel A) shows the time evolution of the mean lesion score of untreated infected mice and of infected mice treated with a single application (given 24 h after the infection) of the poloxamer alone, poloxamer containing 3% foscarnet, poloxamer containing 5% SLS, or poloxamer containing 3% foscarnet+5% SLS. Poloxamer alone did not give any protection against infection. Furthermore, a modest decrease in the mean lesion score was observed in mice treated with poloxamer containing either 5% SLS or 3% foscarnet when compared to untreated infected mice. Of prime interest, in mice treated with the poloxamer containing 3% foscarnet and 5% SLS, we observed a marked and significant reduction ($p<0.05$) in the mean lesion score compared to that of untreated infected mice. The corresponding survival rates for the same treatment groups are given in Panel B which support the results of mean lesion scores. The skin penetration enhancer property of SLS combined with its ability to modify viral infectivity could explain the enhanced efficacy of the foscarnet formulation.

In Vitro Susceptibility of HSV-1 to Combination of Foscarnet and SLS

Figure 22A:
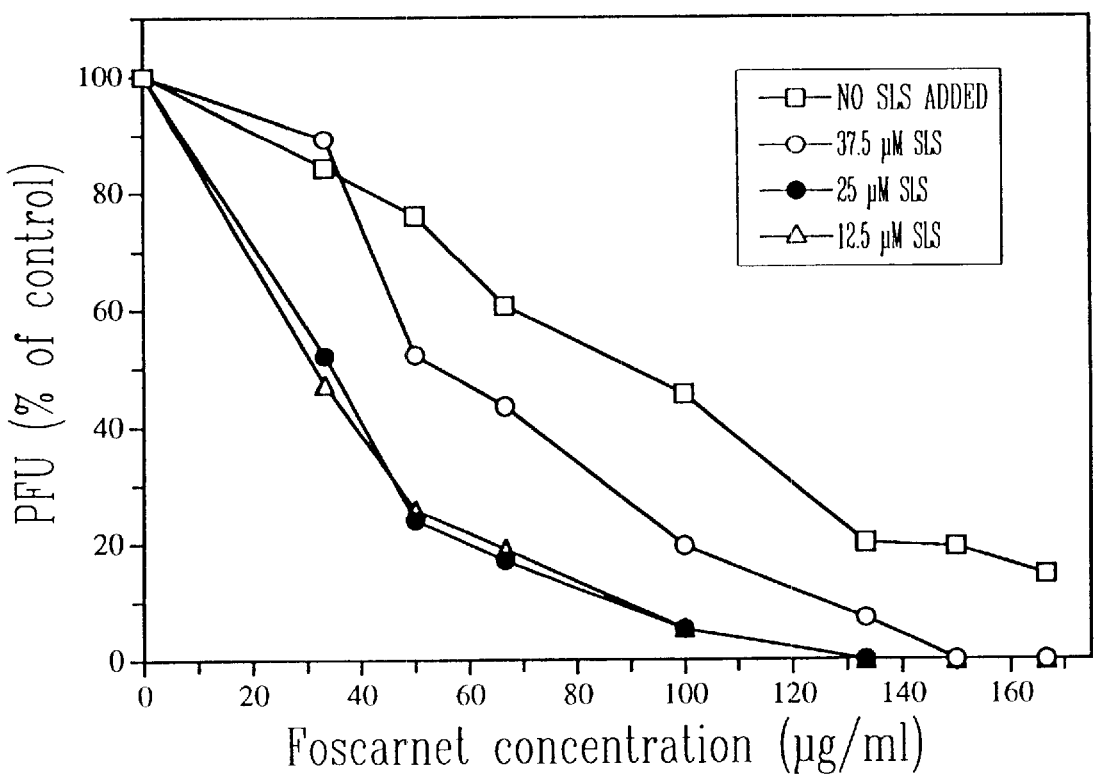
FIG. 22 shows the susceptibility of HSV-1 (strain F) to combinations of different concentrations of foscarnet and SLS in Vero cells. Values are expressed as mean±SD of 3 determinations.
Figure 22B:
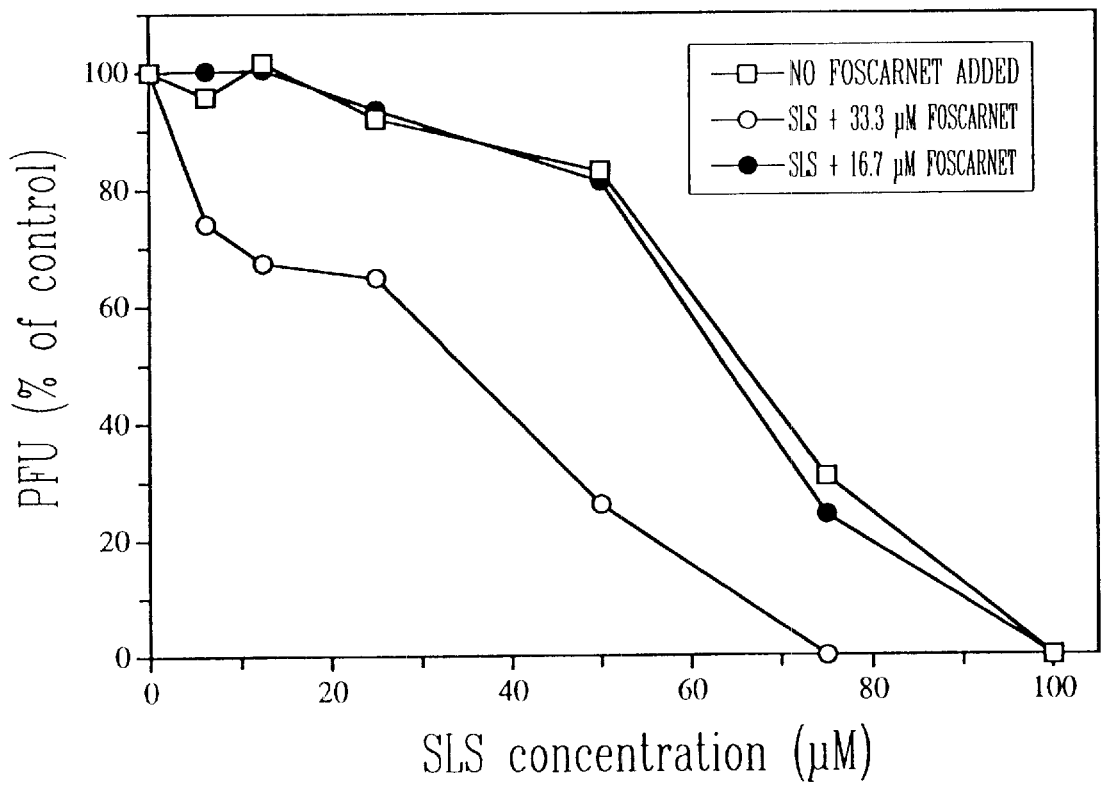

The effect of SLS on the efficacy of foscarnet against HSV-1 (strain F) was investigated in Vero cells. In brief, cells were seeded in 24 well-plates (Costar, Montreal, QC, Canada) and were incubated with HSV-1 strain F (approximately 100 PFU/ml) for 2 h at 37° C. to allow virus adsorption. Afterwards, virus was removed and cells overlaid with 0.5 ml of 0.6% agarose Seaplaque (Marine Colloids, Rockland, Mass.) containing different concentrations of foscarnet, SLS or combination of both compounds. The plates were incubated for 2 days at 37° C. Cells were then fixed with 10% formaldehyde in PBS for 20 min, washed with deionized water and stained with 0.05% methylene blue. Virus susceptibility was evaluated via the determination of PFU. FIG. 22 shows the susceptibility of HSV-1 strain F to combination of different concentrations of foscarnet and SLS on Vero cells. Results show that the presence of SLS enhanced the efficacy of foscarnet against HSV-1 (strain F) in Vero cells.

Potential Applications

The following examples described herein below are specific potential applications of our topical formulations, but are in no way intended to limit the scope thereof. As demonstrated in the above results, our gel formulations could be used for the prevention of infection of skin and/or mucosae and more particularly for the prevention of HSV and HIV. In addition, our results showed that our gel formulations can serve as a prophylactic agent to prevent accidental infection of health care workers. As also demonstrated in the above results, our gel formulations could be used for the treatment and prevention of infection of conditions of skin and/or mucosae and more particularly for the treatment and prevention of herpetic lesions. Beside the above applications, further potential applications are to use our gel formulations i) for the healing and/or treatment of burn wounds and prevention of further infection and ii) for the treatment and/or prevention of infection of ophthalmic conditions. In the above examples, our gel formulations may contain any antimicrobial, bactericidal, virucidal, chemotherapeutic, antiinflammatory, antineoplastic, immunomodulator or any other agent or combination of them which is effective for the treatment and/or prevention of infection and/or abnormal conditions of mucosae and/or skin caused by any pathogen and/or any disease.

The following examples described herein below are specific potential uses of our unique applicator, but are in no way intended to limit the scope thereof. As described above, our applicator could be used for the delivery of any topical formulations used to cover cervical/vaginal/ano-rectal mucosae for the treatment and/or prevention of infection and/or abnormal conditions of mucosae. Our applicator could also be used to deliver i) any topical formulations that can prevent the sexual transmission of pathogens causing STDs, ii) vaginal contraceptive formulations, iii) topical microbicidal formulations against specific diseases and iv) any antimicrobial, bactericidal, virucidal, chemotherapeutic, antiinflammatory, antineoplastic, or immunomodulatory agent, detergents, microbial adsorption inhibitor, skin penetration enhancing agent, cytokine, antigen, vaccines, radioactive agents or combination of them thereof.

What is claimed is:

1. A barrier-forming composition consisting essentially of a poloxamer, a buffer solution and an effective amount of an agent capable of disrupting membrane or protein conformation in a target cell, tissue or mucosa, whereby, when applied to the surface of a person's skin or mucosa, the composition forms a protective semi-solid layer on the skin or mucosa, effective to provide a physical barrier and a chemical barrier against a pathogen, With the proviso that said agent is neither nonoxynol-9, benzalkonium chloride nor menfegol.

2. A barrier-forming composition as defined in claim 1, wherein said agent includes a chaotropic component in an amount sufficient to enhance the disrupting effect towards said pathogen.

3. A barrier-forming composition as defined in claim 1, wherein said agent comprises lauroyl sarcosine or polyoxyethylene 40 stearate.

4. A barrier-forming composition as defined in claim 1, wherein said agent comprises sodium lauryl sulfate or guanidine.

5. A barrier-forming composition as defined in claim 1, wherein said poloxamer is poloxamer 407.

6. A barrier-forming composition as defined in claim 5, wherein said poloxamer 407 is present in a concentration of about 5%–50% (w/w).

7. A barrier-forming composition as defined in claim 5, wherein said poloxamer 407 is present in a concentration of about 15%–35% (w/w).

* * * * *